US008288123B2

(12) United States Patent
Buchanan et al.

(10) Patent No.: US 8,288,123 B2
(45) Date of Patent: Oct. 16, 2012

(54) METHODS AND MEANS RELATING TO PROTEIN VARIANTS

(75) Inventors: Andrew Buchanan, Cambridge (GB); Lutz Jermutus, Cambridge (GB)

(73) Assignee: MedImmune Limited, Cambridge (GB)

( * ) Notice: Subject to any disclaimer, the term of this patent is extended or adjusted under 35 U.S.C. 154(b) by 815 days.

(21) Appl. No.: 11/326,710

(22) Filed: Jan. 5, 2006

(65) Prior Publication Data

US 2006/0183200 A1 Aug. 17, 2006

Related U.S. Application Data

(60) Provisional application No. 60/642,209, filed on Jan. 5, 2005.

(51) Int. Cl.
*C12P 21/02* (2006.01)
*C12N 5/00* (2006.01)
(52) U.S. Cl. ........................ 435/69.1; 435/325
(58) Field of Classification Search .................. None
See application file for complete search history.

(56) References Cited

FOREIGN PATENT DOCUMENTS

GB 2 413 328 10/2005

OTHER PUBLICATIONS

Matsuura T et al: "Selection based on the folding properties of proteins with ribosome display" FEBS Letters, Elsevier, Amsterdam, NL, vol. 539, No. 1-3, Mar. 27, 2003), pp. 24-28.*
Jermutus L et al: "Tailoring in vitro evolution for protein affinity or stability" Proceedings of the National Academy of Sciences of USA, National Academy of Science, Washington, DC, US, vol. 98, No. 1, Jan. 2, 2001, pp. 75-80.*
Coia Get al: "Panning and selection of proteins using ribosome display" Journal of Immunological Methods, Elsevier Science Publishers B.V.,Amsterdam, NL, vot. 254, No. 1-2, Aug. 1, 2001, pp. 191-197.*
Coia et al., Panning and selection of proteins using ribosome display,*J. Immuno. Methods* 254:191-197, 2001.
Chaput & Szostak, Evolutionary Optimization of a Nonbiological ATP Binding Protein for Improved Folding Stability, *Chem. & Biol.* 11:865-874, 2004.
Jermutus et al., Tailoring in vitro evolution for protein affinity or stability, *PNAS* 98(1):75-80, 2001.
Lipovsek & Plückthun, In vitro protein evolution by ribosome display and mRNA display, *J. Immuno. Methods* 290:51-67, 2004.
Matsuura & Plückthun, Selection based on the folding properties of proteins with ribosome display, *FEBS Letters* 539:24-28, 2003.
Sawata & Taira, Modified peptide selection in vitro by introduction of a protein-RNA interaction, *Prot. Eng.* 16(12):1115-1124, 2003.
Wu & Karger, "Hydrophobic Interaction Chromatography of Proteins," *Methods in Enzymology* 270:27-47, 1996.
He et al., "Ribosome Display: Cell-Free Protein Display Technology," *Briefings in Functional Genomics and Proteomics*, vol. 1(2): 204-212, 2002.
Irving et al., "Ribosome Display and Affinity Maturation: From Antibodies to Single V-Domains and Steps Toward Cancer Therapeutics," *J. Immunol. Methods*, 248:31-45, 2001.
Kopsidas, et al., "In Vitro Improvement of a Shark IgNAR Antibody by Qβ Replicase Mutation and Ribosome Display Mimics in vivo Affinity Maturation," *Immunol. Lett.*, 107:163-168, 2006.

* cited by examiner

*Primary Examiner* — Janet Epps-Smith
(74) *Attorney, Agent, or Firm* — Klarquist Sparkman, LLP

(57) ABSTRACT

A method of providing a subject polypeptide variant with improved stability compared with a parent subject polypeptide, employing translation and selection using an RNA expression system, wherein two or more stability selection pressures are applied simultaneously during translation, two or more stability selection pressures are applied simultaneously during selecting, or at least one stability selection pressure is applied during translation and continues to be applied during selecting, and at least one further stability selection pressure is applied during selecting.

41 Claims, 2 Drawing Sheets

SEQUENCE LISTING

<160> NUMBER OF SEQ ID NOS: 16

<210> SEQ ID NO 1
<211> LENGTH: 498
<212> TYPE: DNA
<213> ORGANISM: Homo sapiens
<220> FEATURE:
<221> NAME/KEY: CDS
<222> LOCATION: (1)..(498)

<400> SEQUENCE: 1

```
gcc cca cca cgc ttc atc tgt gac agc cga gtc ctg gag agg tac ctc        48
Ala Pro Pro Arg Phe Ile Cys Asp Ser Arg Val Leu Glu Arg Tyr Leu
1               5                   10                  15 ttg gag gcc aag gag gcc gag aat atc acg acg ggc tgt gct gaa cac        96
Leu Glu Ala Lys Glu Ala Glu Asn Ile Thr Thr Gly Cys Ala Glu His
            20                  25                  30 tgc agc ttg aat gag aat atc act gtc cca gac acc aaa gtt aat ttc       144
Cys Ser Leu Asn Glu Asn Ile Thr Val Pro Asp Thr Lys Val Asn Phe
        35                  40                  45 tat gcc tgg aag agg atg gag gtc ggg cag cag gcc gta gaa gtc tgg       192
Tyr Ala Trp Lys Arg Met Glu Val Gly Gln Gln Ala Val Glu Val Trp
    50                  55                  60 cag ggc ctg gcc ctg ctg tcg gaa gct gtc ctg cgg ggc cag gcc ctg       240
Gln Gly Leu Ala Leu Leu Ser Glu Ala Val Leu Arg Gly Gln Ala Leu
65                  70                  75                  80 ttg gtc aac tct tcc cag ccg tgg gag ccc ctg cag ctg cat gtg gat       288
Leu Val Asn Ser Ser Gln Pro Trp Glu Pro Leu Gln Leu His Val Asp
                85                  90                  95 aaa gcc gtc agt ggc ctt cgc agc ctc acc act ctg ctt cgg gct ctg       336
Lys Ala Val Ser Gly Leu Arg Ser Leu Thr Thr Leu Leu Arg Ala Leu
            100                 105                 110 gga gcc cag gag gaa gcc atc tcc cct cca gat gcg gcc tca gct gct       384
Gly Ala Gln Glu Glu Ala Ile Ser Pro Pro Asp Ala Ala Ser Ala Ala
        115                 120                 125 cca ctc cga aca atc act gct gac act ttc cgc aaa ctc ttc cga gtc       432
Pro Leu Arg Thr Ile Thr Ala Asp Thr Phe Arg Lys Leu Phe Arg Val
    130                 135                 140 tac tcc aat ttc ctc cgg gga aag ctg aag ctg tac aca ggg gag gcc       480
Tyr Ser Asn Phe Leu Arg Gly Lys Leu Lys Leu Tyr Thr Gly Glu Ala
145                 150                 155                 160
```

```
tgc agg aca ggg gac aga                                                498
Cys Arg Thr Gly Asp Arg
            165

<210> SEQ ID NO 2
<211> LENGTH: 166
<212> TYPE: PRT
<213> ORGANISM: Homo sapiens

<400> SEQUENCE: 2

Ala Pro Pro Arg Phe Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Glu Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 3
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 3 gca ccc gcc cgc tcg ccc agc ccc agc acg cag ccc tgg gag cat gtg     48
Ala Pro Ala Arg Ser Pro Ser Pro Ser Thr Gln Pro Trp Glu His Val
1               5                   10                  15 aat gcc atc cag gag gcc cgg cgt ctc ctg aac ctg agt aga gac act     96
Asn Ala Ile Gln Glu Ala Arg Arg Leu Leu Asn Leu Ser Arg Asp Thr
            20                  25                  30 gct gct gag atg aat gaa aca gta gaa gtc atc tca gaa atg ttt gac    144
Ala Ala Glu Met Asn Glu Thr Val Glu Val Ile Ser Glu Met Phe Asp
        35                  40                  45 ctc cag gag ccg acc tgc cta cag acc cgc ctg gag ctg tac aag cag    192
Leu Gln Glu Pro Thr Cys Leu Gln Thr Arg Leu Glu Leu Tyr Lys Gln
    50                  55                  60 ggc ctg cgg ggc agc ctc acc aag ctc aag ggc ccc ttg acc atg atg    240
Gly Leu Arg Gly Ser Leu Thr Lys Leu Lys Gly Pro Leu Thr Met Met
65                  70                  75                  80 gcc agc cac tac aag cag cac tgc cct cca acc ccg gaa act tcc tgt    288
Ala Ser His Tyr Lys Gln His Cys Pro Pro Thr Pro Glu Thr Ser Cys
                85                  90                  95
```

```
gca acc cag att atc acc ttt gaa agt ttc aaa gag aac ctg aag gac    336
Ala Thr Gln Ile Ile Thr Phe Glu Ser Phe Lys Glu Asn Leu Lys Asp
        100                 105                 110 ttt ctg ctt gtc atc ccc ttt gac tgc tgg gag cca gtc cag gag        381
Phe Leu Leu Val Ile Pro Phe Asp Cys Trp Glu Pro Val Gln Glu
    115                 120                 125

<210> SEQ ID NO 4
<211> LENGTH: 127
<212> TYPE: PRT
<213> ORGANISM: Homo sapiens

<400> SEQUENCE: 4

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 5
<211> LENGTH: 522
<212> TYPE: DNA
<213> ORGANISM: Homo sapiens
<220> FEATURE:
<221> NAME/KEY: CDS
<222> LOCATION: (1)..(522)

<400> SEQUENCE: 5 acc ccc ctg ggc cct gcc agc tcc ctg ccc cag agc ttc ctg ctc aag    48
Thr Pro Leu Gly Pro Ala Ser Ser Leu Pro Gln Ser Phe Leu Leu Lys
1               5                   10                  15 tgc tta gag caa gtg agg aag atc cag ggc gat ggc gcg ctc cag        96
Cys Leu Glu Gln Val Arg Lys Ile Gln Gly Asp Gly Ala Ala Leu Gln
            20                  25                  30 gag aag ctg tgt gcc acc tac aag ctg tgc cac ccc gag gag ctg gtg    144
Glu Lys Leu Cys Ala Thr Tyr Lys Leu Cys His Pro Glu Glu Leu Val
        35                  40                  45 ctg ctc gga cac tct ctg gga atc ccc tgg gct ccc ctg agc agc tgc    192
Leu Leu Gly His Ser Leu Gly Ile Pro Trp Ala Pro Leu Ser Ser Cys
    50                  55                  60 ccc agc cag gcc ctg cag ctg gca ggc tgc ttg agc caa ctc cat agc    240
Pro Ser Gln Ala Leu Gln Leu Ala Gly Cys Leu Ser Gln Leu His Ser
65                  70                  75                  80 ggc ctt ttc ctc tac cag ggg ctc ctg cag gcc ctg gaa ggg atc tcc    288
Gly Leu Phe Leu Tyr Gln Gly Leu Leu Gln Ala Leu Glu Gly Ile Ser
                85                  90                  95 ccc gag ttg ggt ccc acc ttg gac aca ctg cag ctg gac gtc gcc gac    336
Pro Glu Leu Gly Pro Thr Leu Asp Thr Leu Gln Leu Asp Val Ala Asp
            100                 105                 110 ttt gcc acc acc atc tgg cag cag atg gaa gaa ctg gga atg gcc cct    384
```

```
Phe Ala Thr Thr Ile Trp Gln Gln Met Glu Glu Leu Gly Met Ala Pro
        115                 120                 125 gcc ctg cag ccc acc cag ggt gcc atg ccg gcc ttc gcc tct gct ttc      432
Ala Leu Gln Pro Thr Gln Gly Ala Met Pro Ala Phe Ala Ser Ala Phe
        130                 135                 140 cag cgc cgg gca gga ggg gtc ctg gtt gcc tcc cat ctg cag agc ttc      480
Gln Arg Arg Ala Gly Gly Val Leu Val Ala Ser His Leu Gln Ser Phe
145                 150                 155                 160 ctg gag gtg tcg tac cgc gtt cta cgc cac ctt gcc cag ccc              522
Leu Glu Val Ser Tyr Arg Val Leu Arg His Leu Ala Gln Pro
                165                 170

<210> SEQ ID NO 6
<211> LENGTH: 174
<212> TYPE: PRT
<213> ORGANISM: Homo sapiens

<400> SEQUENCE: 6

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 7
<211> LENGTH: 498
<212> TYPE: DNA
<213> ORGANISM: Homo sapiens

<400> SEQUENCE: 7
tctgtcccct gtcctgcagg cctccctgt gtacagcttc agctttcccc ggaggaaatt      60
ggagtagact cggaagagtt tgcggaaagt gtcagcagtg attgttcgga gtggagcagc    120
tgaggccgca tctggagggg agatggcttc ctcctgggct cccagagccc gaagcagagt    180
ggtgaggctg cgaaggccac tgacggcttt atccacatgc agctgcaggg gctcccacgg    240
ctgggaagag ttgaccaaca gggcctggcc ccgcaggaca gcttccgaca gcagggccag    300
gccctgccag acttctacgg cctgctgccc gacctccatc ctcttccagg catagaaatt    360
aactttggtg tctgggacag tgatattctc attcaagctg cagtgttcag cacagcccgt    420
cgtgatattc tcggcctcct tggcctccaa gaggtacctc tccaggactc ggctgtcaca    480
```

-continued gatgaagcgt ggtggggc         498

<210> SEQ ID NO 8
<211> LENGTH: 381
<212> TYPE: DNA
<213> ORGANISM: Homo sapiens

<400> SEQUENCE: 8
ctcctggact ggctcccagc agtcaaaggg gatgacaagc agaaagtcct tcaggttctc         60
tttgaaactt tcaaaggtga taatctgggt tgcacaggaa gtttccgggg ttggagggca        120
gtgctgcttg tagtggctgg ccatcatggt caagggcccc ttgagcttgg tgaggctgcc        180
ccgcaggccc tgcttgtaca gctccaggcg ggtctgtagg caggtcggct cctggaggtc        240
aaacatttct gagatgactt ctactgtttc attcatctca gcagcagtgt ctctactcag        300
gttcaggaga cgccgggcct cctggatggc attcacatgc tcccagggct gcgtgctggg        360
gctgggcgag cgggcgggtg c        381

<210> SEQ ID NO 9
<211> LENGTH: 522
<212> TYPE: DNA
<213> ORGANISM: Homo sapiens

<400> SEQUENCE: 9
gggctgggca aggtggcgta gaacgcggta cgacacctcc aggaagctct gcagatggga         60
ggcaaccagg accctcctg cccggcgctg gaaagcagag gcgaaggccg gcatggcacc        120
ctgggtgggc tgcagggcag gggccattcc cagttcttcc atctgctgcc agatggtggt        180
ggcaaagtcg gcgacgtcca gctgcagtgt gtccaaggtg ggacccaact cgggggagat        240 ccccttccagg gcctgcagga gcccctggta gaggaaaagg ccgctatgga gttggctcaa        300
gcagcctgcc agctgcaggg cctggctggg gcagctgctc aggggagccc aggggatgcc        360
cagagagtgt ccgagcagca ccagctcctc ggggtggcac agcttgtagg tgcacacag         420 cttctcctgg agcgctgcgc catcgccctg gatcttcctc acttgctcta agcacttgag        480
caggaagctc tggggcaggg agctggcagg gcccaggggg gt        522

<210> SEQ ID NO 10
<211> LENGTH: 166
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 2

<400> SEQUENCE: 10

Ala Pro Pro Arg Phe Ile Cys Asp Ser Arg Val Leu Glu Arg Tyr Ile
1               5                   10                  15

Leu Glu Ala Lys Glu Ala Glu Asn Phe Thr Met Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Ala Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu

```
                100             105             110
Gly Ala Gln Glu Glu Ala Ile Ser Pro Pro Asp Ala Ala Ser Ala Ala
            115                 120                 125

Pro Leu Arg Thr Ile Thr Ala Asp Thr Phe His Lys Leu Phe Arg Val
        130                 135             140

Tyr Ser Asn Phe Leu Arg Gly Lys Leu Lys Leu Tyr Val Gly Glu Ala
145                 150                 155                 160

Cys Arg Thr Gly Asp Arg
                165

<210> SEQ ID NO 11
<211> LENGTH: 166
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 2

<400> SEQUENCE: 11

Ala Pro Pro Arg Phe Ile Cys Val Ser Arg Val Leu Glu Arg Tyr Leu
1               5                   10                  15

Leu Glu Ala Lys Glu Ala Glu Asn Ile Ala Ala Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Glu Glu Ala Ile Ser Pro Pro Asp Ala Ala Pro Ala Ala
            115                 120                 125

Pro Leu Arg Thr Ile Thr Ala Asp Thr Phe Arg Lys Leu Phe Arg Val
        130                 135             140

Tyr Ser Asn Phe Leu Arg Gly Lys Leu Lys Leu Tyr Thr Glu Glu Ala
145                 150                 155                 160

Cys Arg Thr Gly Asp Arg
                165

<210> SEQ ID NO 12
<211> LENGTH: 166
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 2

<400> SEQUENCE: 12

Ala Pro Pro Arg Phe Ile Cys Val Ser Arg Val Leu Glu Arg Tyr Leu
1               5                   10                  15

Leu Glu Ala Lys Glu Ala Glu Asn Ile Thr Ala Gly Cys Ala Glu His
            20                  25                  30

Cys Ser Leu Asn Glu Asn Ile Thr Val Pro Asp Thr Lys Val Asn Phe
        35                  40                  45

Asn Ala Trp Lys Arg Met Glu Val Gly Gln Gln Ala Val Glu Val Arg
    50                  55                  60
```

```
Gln Gly Leu Ala Leu Leu Ser Glu Ala Val Leu Arg Gly Gln Ala Leu
 65                  70                  75                  80

Leu Ala Asn Ser Ser Gln Pro Trp Gly Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Glu Glu Ala Ile Ser Pro Pro Asp Ala Ala Pro Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Glu Glu Ala
145                 150                 155                 160

Cys Arg Thr Gly Asp Arg
                165

<210> SEQ ID NO 13
<211> LENGTH: 166
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 2

<400> SEQUENCE: 13

Ala Pro Pro Arg Phe Ile Cys Asp Ser Arg Val Leu Glu Arg Tyr Leu
 1               5                  10                  15

Leu Glu Ala Lys Glu Ala Glu Asn Ile Ala Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Arg
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Glu Glu Ala Ile Ser Pro Pro Asp Ala Ala Ser Ala Ala
        115                 120                 125

Pro Leu Arg Thr Ile Thr Val Asp Thr Phe Arg Lys Leu Phe Arg Val
    130                 135                 140

Tyr Ser Asn Phe Leu Arg Gly Lys Leu Lys Leu Tyr Thr Glu Glu Ala
145                 150                 155                 160

Cys Arg Thr Gly Asp Arg
                165

<210> SEQ ID NO 14
<211> LENGTH: 166
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 2

<400> SEQUENCE: 14

Ala Pro Pro Arg Phe Ile Cys Val Ser Arg Val Leu Glu Arg Tyr Leu
 1               5                  10                  15
```

```
Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Phe Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Ala Leu Leu Arg Ala Leu
            100                 105                 110

Gly Ala Gln Glu Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asp Phe Leu Arg Gly Lys Leu Lys Leu Tyr Thr Gly Glu Ala
145                 150                 155                 160

Cys Arg Thr Gly Asp Arg
                165

<210> SEQ ID NO 15
<211> LENGTH: 127
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 4

<400> SEQUENCE: 15

Ala Pro Ala Ser Ser Pro Ser Pro Ser Thr Gln Pro Trp Glu Leu Val
1               5                  10                  15

Asn Val Ile Gln Glu Ala Arg Arg Leu Leu Asn Leu Ser Arg Asp Thr
             20                  25                  30

Ala Ala Glu Met Asn Glu Thr Val Glu Val Val Ser Glu Met Phe Asp
         35                  40                  45

Leu Gln Glu Pro Thr Cys Leu Gln Thr Arg Leu Glu Leu Tyr Thr Gln
     50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Ala Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 16
<211> LENGTH: 174
<212> TYPE: PRT
<213> ORGANISM: Artificial sequence
<220> FEATURE:
<223> OTHER INFORMATION: Polypeptide variant comprising a set of
      mutations in the human wild-type sequence of SEQ ID NO: 6

<400> SEQUENCE: 16

Thr Pro Leu Gly Pro Ala Ser Ser Leu Pro Gln Ser Phe Leu Leu Lys
1               5                  10                  15

Gly Leu Glu Gln Val Arg Lys Ile Gln Gly Asp Gly Ala Ala Leu Gln
```

-continued

```
                 20                  25                  30
Glu Lys Leu Cys Ala Thr Tyr Lys Leu Cys His Pro Glu Glu Leu Val
            35                  40                  45

Leu Leu Gly His Ser Leu Gly Ile Pro Arg Ala Pro Leu Ser Ser Cys
        50                  55                  60

Pro Ser Gln Ala Leu Arg Leu Ala Gly Cys Leu Ser Gln Leu His Ser
65                      70                  75                  80

Gly Leu Leu Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

METHODS AND MEANS RELATING TO PROTEIN VARIANTS

This application claims the benefit of U.S. Provisional Application No. 60/642,209, filed Jan. 5, 2005. The entire disclosure of that application is incorporated herein in its entirety.

The present invention relates to methods for selecting, obtaining or producing polypeptide variants with improved stability. It further relates to manufacture and use of the variants following selection, for example in therapy.

The invention employs use of display technology incorporating in vitro translation and covalent or non-covalent linkage between genotype, such as RNA, and the encoded phenotype, such as a polypeptide of interest, to select for polypeptide variants that have improved stability compared with a parent polypeptide and that retain functional activity.

Ribosome or polysome display and selection involves construction of nucleic acid libraries, screening for binding, and identification of binding entities of interest. The library is made by synthesising a DNA pool of diverse sequences that are then transcribed to produce a pool of mRNAs. In vitro translation is used to generate the encoded polypeptides or proteins displayed, and desirable binding interactions are selected using immobilised target antigen. mRNA encoding the binding entities can be used to make cDNA, which can then be amplified and the process may be repeated to enrich the population for genes encoding binders. The selected proteins may later be identified by cloning individual coding sequences and DNA sequencing.

The technology has been reviewed extensively (Hanes et al., (2000) Meth. Enzymol. 328, 403-430; Plückthun et al., (2000) Adv. Prot. Chem. 55, 367-403; Lipovsek and Plückthun (2004) J. Immunological Methods 290, 51-67).

The technology has been used for the display of antibody fragments, peptides and various proteins, including periplasmic and cytoplasmic proteins such as β-lactamase and ankyrin-repeat proteins.

Recovery of mRNA from polysome complexes was first reported in 1973 in a paper describing a protocol to capture mRNA coding for a mouse immunoglobulin L-chain using antibodies and immobilised oligothymidine (Schechter (1973) PNAS USA 70, 2256-2260). Improvements to the polysome immunoprecipitation protocols were made by Payvar and Schimke (Eur. J. Biochem. (1979) 101, 271-282) and cDNA clones for the heavy chain of HLA-DR antigens were obtained after immunoprecipitation of polysomes using a monoclonal antibody (PNAS USA (1982) 79, 1844-1848). Production of libraries of antibodies by ribosome display was proposed and patented by Kawasaki (U.S. Pat. No. 5,643,768 and U.S. Pat. No. 5,658,754, EP-B-0494955).

There have been various examples of the use of ribosome display using either eukaryotic or prokaryotic translation systems. The first demonstration of selection of peptide ligands using an E. coli extract was by Mattheakis et al., (PNAS USA (1994) 91, 9022-9026 and Methods Enzymol (1996) 267, 195-207). This group demonstrated selection of peptide ligands that are similar to known peptides epitopes of a given antibody, using the antibody as a selection substrate. High-affinity peptide ligands which bind prostate-specific antigen have been identified using polysome selection from peptide libraries using a wheat germ extract translation system (Gersuk et al., (1997) Biotech and Biophys. Res. Com. 232, 578-582). The selection of functional antibody fragments was reported using an E. coli translation system designed for increased yield of ternary complexes and allowing disulphide bond formation (Hanes and Pluckthun, PNAS USA (1997) 94, 4937-4942). This experimental set up has subsequently been used to select antibodies from a murine library, and it was shown that affinity maturation occurs during the selection due to the combined effect of PCR errors and selection. A scFv fragment with a dissociation constant of about $10^{-11}$ M was obtained (Hanes et al., PNAS USA (1998) 95, 14130-50). Enrichment for specific of antibodies from mixed populations using rabbit reticulyocyte lysate extracts has also been demonstrated (He and Taussig (1997) NAR, 5132-5234).

mRNA display, like ribosome display, uses a complex between mRNA and the encoded polypeptide as the basic selection unit. What distinguishes mRNA display from ribosome display is the covalent nature of the linkage between the mRNA and the protein. The linkage is achieved through a small adaptor molecule, typically puromycin (Nemoto et al., (1997) FEBS Lett 414:405; Roberts and Szostak, (1997) Proc. Natl. Acad. Sci. USA 94: 12297; Takahashi et al., (2003) Trends Biochem. Sci. 28:159). mRNA display is not limited to 4° C., which is the usual temperature at which ribosome display is carried out. Typically the temperature at which selections are performed is limited by the stability of the protein target. mRNA display has been used for affinity selections of peptides and antibodies (Reviewed in Lipovsek and Plückthun, (2004) J Immunological Methods 290:51-97).

The present invention provides methodology that is applicable to display technology incorporating in vitro translation and covalent or non-covalent linkage between genotype, such as RNA, and the encoded phenotype, such as a polypeptide of interest, for selection of subject polypeptide variants with improved stability and retained functionality compared with a parent polypeptide. Methods of the invention incorporate a number of features not previously used together in ribosome or mRNA display.

In embodiments of the present invention, two or more than two stability selection pressures are employed, simultaneously, especially two or more than two stability selection pressures, allowing for selection of stable polypeptides.

A stability selection pressure may be any factor that can be used in display technology incorporating in vitro translation and covalent or non-covalent linkage between genotype, such as RNA, and the encoded phenotype, such as a polypeptide of interest, that allows for selection of a variant polypeptide on the basis of its stability. Stability can generally be defined as the propensity of a molecule to exist in its folded and active state. A stability selection pressure may disrupt or prevent a polypeptide folding correctly such that it does not attain an active or fully active state. A stability selection pressure may affect the ability of a polypeptide to remain in its folded and active state. A stability selection pressure may differentiate in some way between polypeptides that are in a folded and active state and those that are not.

For example, a stability selection pressure may be a chemical denaturant, such as urea, guanidine HCl (GuHCl) or thiocyanate, for example, sodium thiocyanate. A stability selection pressure may be a reducing agent, such as dithiothreitol (DTT), Tris[2-carboxyethyl]phosphine hydrochloride (TCEP), mercaptoethanol or glutathione. A stability selection pressure may be a physical denaturant, such as pH or temperature, in particular increased temperature. A selection pressure may be a protease or enzyme capable of degrading protein. A selection pressure may be depletion of chaperons or small molecule protein folding inhibitors.

A stability selection pressure may be the use of hydrophobic interaction chromatography (HIC).

Hydrophobic interaction chromatography (HIC) is a technique for the separation of biomolecules based on differences in their surface hydrophobicity. HIC techniques have been used as a part of protein purification strategies as well as an analytical tool for the detection of protein conformational changes (reviewed in Queiroz et al., (2001) J. Biotech. 87, 143-159; Fulton and Vanderburgh (1996) Biomolecule Chromatography PerSeptive Biosystems). HIC is based on hydrophobic attraction between the HIC matrix and the protein molecules. The HIC matrix consists of small non-polar groups (butyl, octyl or phenyl) attached to a hydrophilic polymer backbone (e.g. cross-linked dextran or agarose). Many proteins, generally considered to be hydrophilic, also have sufficient numbers of hydrophobic groups allowing interaction with the HIC matrix. HIC is sensitive enough to interact with non-polar groups normally buried within the tertiary structure of the protein but exposed due to incorrect folding. The strength of the interaction is dependent upon the type of matrix, type and concentration of salt, pH, additives and temperature.

The present inventors' work described herein demonstrates for the first time use of at least two selection pressures, such as DTT, HIC and increased temperature, simultaneously to improve the pharmacological properties of therapeutic proteins using display technology such as ribosome or mRNA display, in particular to improve shelf-life stability.

Among the advantages of using at least two selection pressures, especially simultaneously, compared with single or sequential selection pressures, is that the strategy is more generic and robust. From the inventors' experience some proteins are not susceptible to one selection pressure alone, i.e. are not significantly destabilised by one pressure alone, but are susceptible to two pressures, especially when applied simultaneously. For example, the inventors have seen that DTT may be insufficient on its own and is useful only for certain types of protein, for example, those with disulphide linkages. Thus, the present invention using selection allows for a more stringent selection method and the selection of any protein on the basis of stability.

In methods of the invention, a library of genes encoding polypeptide variants may be constructed. Polypeptide variants may be subject to a stability selection pressure as they are produced, for example by translating them in the presence of DTT. A stability selection pressure may act during translation of a polypeptide, during folding of a nascent polypeptide and/or following folding of a polypeptide.

A stability selection pressure that may be used while a polypeptide is produced, that is during translation and folding of the nascent polypeptide, includes DTT, glutathione, Tris [2-carboxyethyl]phosphine hydrochloride (TCEP), mercaptoethanol, urea, guanidine HCl (GuHCl), depletion of chaperons, pH, and small molecule protein folding inhibitors. Chaperons act to aid folding of a polypeptide. Their depletion thus affects the ability of a polypeptide to fold correctly. Chaperones can be depleted from cell-free extracts by using immunoprecipitation (IP). Antibodies against all major chaperons such as GroEL/GroES, DnaJ, DnaK are available commercially and could be used for IP-based removal of specific components of a ribosome display system. The same approach has been demonstrated for the removal of phosphatases from cell-free abstracts which improved the abundance of ATP and in consequence expression yield (Shen et al. (1998) Biochem. Eng. J. 2:23-28). Also, folding may be inhibited by specifically designed small molecules (Gestwicki et al. (2004) Science 306:865-869). A small molecule protein folding inhibitor may be any small molecule that is capable of disrupting or preventing correct folding of a protein.

Two selection pressures are applied simultaneously within the overall process of producing the variants (e.g. during translation) and selection (e.g. by binding or biological activity). Preferably one or more than one selection pressure is applied during the selection part of the process, more preferably two selection pressures in the selection part or more than two. There may be one or more than one selection pressure in the translation part of the process and one or more than one selection pressure in the selection part of the process.

Selection is made for variants that are more stable and still bind their cognate ligand, receptor or specific binding pair member. Variants are incubated with two or more than two stability selection pressures simultaneously. In methods of the invention, the stability selection pressures used, preferably used simultaneously, may be for example, HIC and increased temperature. Improved, active variants are captured via their cognate ligand, receptor or specific binding pair member. The selection pressures may be present during capture of active variants or may be removed prior to incubation of variants with their cognate ligand, receptor or specific binding pair member.

Stability selection pressures that may be used include DTT, glutathione, TCEP, mercaptoethanol, urea, GuHCl, sodium thiocyanate, proteases, HIC and increased temperature.

HIC may use a hydrophobic interaction chromatography matrix or any other suitable hydrophobic matrix, for example, a matrix that is used for reverse phase chromatography. For example, a suitable matrix for HIC is butyl-Sepharose™ (Amersham).

By "increased temperature" is meant a temperature that is higher than the temperature at which the display technique is usually carried out and which is at least partly destabilising for proteins For example, as described herein, ribosome display is usually carried out at 4° C. to ensure the stability of the ribosome/mRNA/polypeptide complex. Thus, increased temperature in a method using ribosome display is a temperature above 4° C. For example, increased temperature may be above 15° C., or at or above room temperature, by which is meant any temperature between about 20° C. and about 30° C. inclusive. An increased temperature may be or be about 20, 21, 22, 23, 24, 25, 26, 27, 28, 29 or 30° C. Preferably, an increased temperature is or is about 25° C. Preferably, a method of the invention uses HIC carried out at room temperature, preferably at about 25° C.

Also as described herein, mRNA display is usually carried out at about 25° C. Thus, an increased temperature in a method using mRNA display is a temperature above 25° C. Such a temperature may be or be within 25-30° C., 25-35° C. 30-35° C., 25-40° C., 30-40° C., 35-40° C., 25-50° C., 30-50° C., or 35-50° C., or may be or be about 25, 30, 35, 40, 45 or 50° C.

Preferably, an increased temperature is at least 20° C. higher than the usual operating temperature of a display method in order to serve as a stability selection pressure.

The use of the reducing agent DTT as a selection pressure in ribosome display to improve the stability of proteins with disulphide bridges is disclosed in Jermutus et al., (2001) Proc Natl Acad Sci USA 98: 75-80.

The use of HIC for the removal of unfolded and misfolded peptides from a random-sequence library prior to selection is disclosed by Keefe and Szostak (2001) Nature 410: 715-718, and Matsuura and Pluckthun (2003) FEBS Letters 539: 24-38.

The use of proteases as a selection pressure has been described (Matsuura and Plückthun 2004 FEBS Letters 539: 24-38).

The use of mRNA display using GuHCl at 25° C. is described in Chaput and Szostak (2004) Chem Biol 11: 865-874.

Thus, selection pressures have been used in ribosome and mRNA display, either alone or sequentially. However, the present invention employs for the first time use of two or more stability selection pressures in display technology incorporating in vitro translation and covalent or non-covalent linkage between genotype, such as RNA, and the encoded phenotype, such as a polypeptide of interest.

In accordance with the present invention, the selection protocol differs from the usual in ribosome or mRNA display.

For example, ribosome display selections are carried out at 4° C. to ensure the stability of the ribosome/mRNA/protein complexes (Hanes et al., (2000) Meth Enzymol 328:404). However, HIC is temperature dependent and higher temperature increases the hydrophobic interaction between the HIC matrix and protein. In order to maximise the HIC selection pressure, incubation with HIC matrix in accordance with embodiments of the present invention is performed at room temperature. Thus, two selection pressures of HIC and increased temperature may be used in combination to select for stable polypeptide variants. It was unexpected to find that the ribosome complexes were stable at room temperature, making such a selection protocol possible.

The present invention also provides selection protocols using three stability selection pressures, for example, DTT, HIC and increased temperature.

Selection pressures may act during folding of the nascent polypeptide and/or on the folded protein.

Those pressures which act on the folding polypeptide and may not be effective on the folded molecule, should be added during translation and then maintained during post translation. These include DTT, glutathione, TCEP, sodium thiocyanate, mercaptoethanol, urea, GuHCL, pH, small molecule folding inhibitors and depleted chaperons.

Those pressures that destabilise the folded protein, could be added during translation or restricted to the post translational step. These include urea, GuHCL, HIC, temperature and proteases.

Proof of usefulness and effectiveness of the present invention is illustrated with reference to provision of new variants of human erythropoietin (EPO), granulocyte macrophage colony stimulating factor (GM-CSF) and granulocyte colony stimulating factor (G-CSF).

Human EPO was first cloned and amino acid sequence reported by Lin et al., Proc Natl Acad Sci USA (1985) 82: 7582-4 and Jacobs K et al., Nature 313: 806-810 (1985).

EPO is a major biopharmaceutical product with worldwide sales topping US$ 3 billion. It is used primarily to boost erythrocyte and red blood cell formation in patients to treat anaemia associated with chronic renal failure, cancer chemotherapy, HIV infection, pediatric use, premature infants and to reduce the need for blood transfusions in anaemic patients undergoing elective non-cardiac and non-vascular surgery.

Human EPO is an acidic glycoprotein with a molecular weight of approximately 30400 daltons. It is composed of an invariant 165 amino acid single polypeptide chain containing four cysteine residues (at positions 7, 29, 33 and 161), which form the internal disulphide bonds (Lai et al., J Biol Chem 1986 261: 3116-3121; Recny et al., J Biol Chem 1987 262: 17156-17163). The disulphide bridge between cysteine 7 and 161 is known to be essential for biological activity. The carbohydrate portion of EPO consists of three N-linked sugars chains at Asn 24, 38 and 83, and one O-linked sugar at Ser 126 (Browne J K et al., Cold spring Harb symp Quant Biol 1986 51: 693-702 Egrie J C et al., Immunobiology 1986 172: 213-224.)

The structure of human EPO has been reported (Cheetham et al., 1988 Nat Struct Biol 5:861-866; Syed et al., 1998 Nature 395:511-516). Human EPO is a four helix bundle, typical of members of the hematopoietic growth factor family. In contrast to the invariant amino acid sequence, the carbohydrate structures are variable, a feature referred to as micro-heterogeneity. The differences in carbohydrate moieties, in terms of the branching pattern, complexity size and charge has profound effects on the pharmacokinetics and pharamacodynamics of EPO. The effects of different glycoslyation patterns have been well studied (Darling et al., 2002 Biochemistry 41: 14524-14531; Storring et al., 1998 Br J Haematol 100: 79-89; Halstenson et al., 1991 Clin Pharmacol Ther 50: 702-712; Takeuchi et al., 1990 J Biol Chem 265: 12127-12130).

Granulocyte-macrophage colony stimulating factor (GM-CSF) is a cytokine that regulates the production, effector cell function and survival of myeloid cells.

Human GM-CSF is used in myeloid reconstitution following bone marrow transplant, bone marrow transplant engraftment failure or delay, mobilization and following transplantation of autologous peripheral blood progenitor cells, and following induction chemotherapy in older adults with acute myelogenous leukemia. GM-CSF is available under the names leukine (Amgen) and leucomax (Schering-Plough).

Human GM-CSF was first cloned and amino acid sequence reported by Cantrell et al., Cloning, sequence, and expression of a human granulocyte/macrophage colony-stimulating factor. Proc Natl Acad Sci USA. (September 1985); 82(18): 6250-4.

GM-CSF is a monomeric protein of 127 amino acids with two glycosylation sites. The protein is synthesized as a precursor of 144 amino acids, which includes a hydrophobic secretory signal sequence at the amino terminal end. GM-CSF produced in mammalian cells is found in different glycosylation forms varying in size from 14-35 KDa. The sugar moiety is not required for the spectrum of biological activities. The structure of GM-CSF is a four helix bundle (Diederichs, K., Boone, T. & Karplus, P. A. (1991). Novel fold and putative receptor binding site of granulocyte-macrophage colony-stimulating factor. Science, 254, 1779-1782), similar to other four helical cytokines. It encodes four cysteine residues that form two disulphide bridges (positions 54/96 and 88/121).

Human G-CSF is used to decrease the incidence of infection related to febrile neutopenia (loss of neutrophils) in patients receiving myelosuppressive cancer chemotherapy drugs associated with a significant incidence of severe neutopenia with fever. The use of a G-CSF product helps physicians deliver planned chemotherapy doses on time and improve clinical outcomes. G-CSF is available under the trade names Neupogen, Neulasta (pegylated G-CSF) and Granocyte.

Human G-SCF was first cloned and expressed by Nagata et al., The chromosomal gene structure and two mRNAs for human granulocytes colony stimulating factor Nature 5: 575-581 (1986).

Mature G-CSF is monomer protein of 174 amino acids with one O-gylcosyaltion site at Thr133, two intra molecular disulphide bridges (Cys36-Cys42 and Cys65-Cys74). The structure of G-CSF is a four helix bundle (Hill et al 1993 Proc Natl Acad Sci USA 90; 5167-5171). Gylcosylation contributes to the stability of the molecule but is not required for biological activity (Oh-eda et al. 1990 J Biol Chem 265:

11432-11435). Recombinant G-CSF is produced in *Escherichia coli*, inclusion bodies harvested and the G-CSF refolded (U.S. Pat. No. 5,849,883).

There are a number of reports of G-CSF variants with improved stability e.g. Bishop et al. 2001 Reengineering Granulocyte colony-stimulating factor for enhanced stability J Biol Chem 276: 33465-33470; Lou et al 2002 Development of a cytokine analog with enhance stability using computational ultrahigh throughput screening Protein Science 11: 1218-1226; Fuji et al 1997 Structure of KW-228, a tailored human granulocyte colony stimulating factor with enhanced biological activity and stability FEBS Letters 410: 131-135.

However all reports of G-CSF *E. coli* production use cytoplasmic expression, producing inclusion bodies from which G-CSF is refolded. There are no reports of successful soluble expression of human G-CSF in *E. coli* except for one using a Bacillus signal peptide, histadine hexamer and factor Xa cleavage site (Jeong and Lee 2001 Protein Expression and Purification 23:311-318). This resulted in soluble expression but with N terminal histidine tag, which was not cleaved and no biological activity was demonstrated.

A G-CSF variant when expressed in *E. coli* produces soluble, monomeric and active protein. This enables a simplified expression and purification procedure without the need for refolding steps. This optimises the preparation and may have benefits for efficacy and storage properties.

The present invention provides methods demonstrated herein to provide EPO, GM-CSF and G-CSF variants with improved stability, which translates into benefits for patient and manufacturer. Variants with improved stability generally provide for a higher expression and higher yield in downstream processing which results in improved cost of goods (COG). Further, variants with improved stability have an improved shelf life. Longer shelf life is beneficial as it also influences the cost of goods. A further benefit is reduced need for cold storage, assisting distribution and patients who self-administer at home.

A variant with improved stability may have increased efficacy in the body, resulting from a longer half-life. Further, a variant with improved stability may be more amenable to routes of administration such as subcutaneous administration, because of reduced aggregation, which not only increases efficacy but also reduces the risk of neutralising or binding antibodies being elicited.

The invention is equally applicable to other polypeptides and to selection of polypeptide variants of improved stability.

As described herein, use of multiple selection pressures, especially with simultaneous application, allows for a more generic selection protocol applicable to the selection of any polypeptide on the basis of stability. Preferred features of a polypeptide to be the subject of this invention are described herein. A polypeptide subject to the invention should be able to be displayed using display technology incorporating in vitro translation and covalent or non-covalent linkage between genotype, such as RNA, and the encoded phenotype, such as polypeptide of interest. A polypeptide therefore needs to be translatable in a cell-free expression system, as well as able to fold into its correct tertiary structure in such a system.

A polypeptide subject to the invention may be monocistronic or consist of identical sub-units (homo-multimeric). A bimeric molecule fused into one polypeptide chain may be employed, expressed from a single cistron, e.g. a single chain Fv antibody molecule. A polypeptide preferably contains cysteine residues that may form disulphide bonds, or other residues that are important for folding and stability. Elements of a polypeptide that are important for folding and stability can preferably be removed or affected depending on conditions, for example by addition of reducing agents, or by site-directed mutagenesis.

Examples of proteins subject to the present invention further include but are not limited to members of the family of four anti-parallel α-helix bundle proteins, such as interferons or interleukins, as well as the extra-cellular domain of complex receptors, such as tumour necrosis factor receptor II (TNFRII).

Stability can generally be defined as the propensity of the molecule to remain in its folded and active state. Naturally occurring molecules are usually of limited stability as their metabolism, and often their fast metabolism, is a key characteristic of their intrinsic mechanism of action in the body.

Usually, a stable protein in its folded and native structure cannot be degraded by proteases or other mechanisms. It is due to two key off pathways from the stable state by which proteins are usually eliminated in the body. These two are unfolding and aggregation. They are usually linked. Unfolding is the pathway of reverting the folded active molecule into a less folded state. Aggregation is the result of misfolding such that the molecule irreversibly turns into a non-active state. Both unfolding and aggregation significantly increase the protein's susceptibility to proteolytic or other digestion.

Protein aggregation is a major draw back with the *E. coli* expression of recombinant proteins in a soluble functional form. Aggregation of recombinant proteins is probably due to a limiting amount of chaperons. Under these conditions folding is not complete and partially folded intermediates with exposed hydrophobic surfaces go off-pathway and self associate. The self-association is the basis for protein aggregation and the formation of inclusion bodies (see review Baneyx (1999) Recombinant protein expression in *Escherichiia coli*. Curr Opin Biotechnol 10:411-421; Carrio and Villaverde (2002) J Biotech 96, 3-12; Geogiou and Valaw (1996) Curr Opin Biotech 7, 190-197).

GM-CSF expressed cytoplasmically in *E. coli* is known to form insoluble aggregates (Greenberg et al., (1988) Curr Microbiol 17:321-332). Periplasmic expression also results in the majority of the product in the insoluble fraction (Lundell et al., (1990) Biotechnology and Applied Biochemistry 12:567-578).

The generation of more stable variants of a protein that is prone to aggregation during expression could result in soluble monomeric protein. Such a protein may fold more efficiently, be less likely to unfold and thus have fewer exposed hydrophobic surfaces that would result in aggregation. This would increase the yield from *E. coli* expression and remove the need for refolding processes.

Various attempts to improve soluble expression of proteins have been made. —For example, modification of culture conditions, use of chaperons, generation of fusion proteins and engineering, use of GuHCl selections, have been used with varying degrees of success.

In methods in accordance with embodiments of the present invention the folding and unfolding pathway of the subject polypeptide is altered such that the resulting entity is more stable. While the evolution of increased thermodynamic stability of proteins has been demonstrated previously (Jermutus et al., (2001) Proc Natl Acad Sci 98: 75-80) this is the first description that in vitro evolution and the resulting amino acid changes from this process can result in tangible benefits of bio-therapeutics.

Embodiments of the invention are now described in more detail, by way of example only and not by limitation, including reference to the figures.

Figure 1:
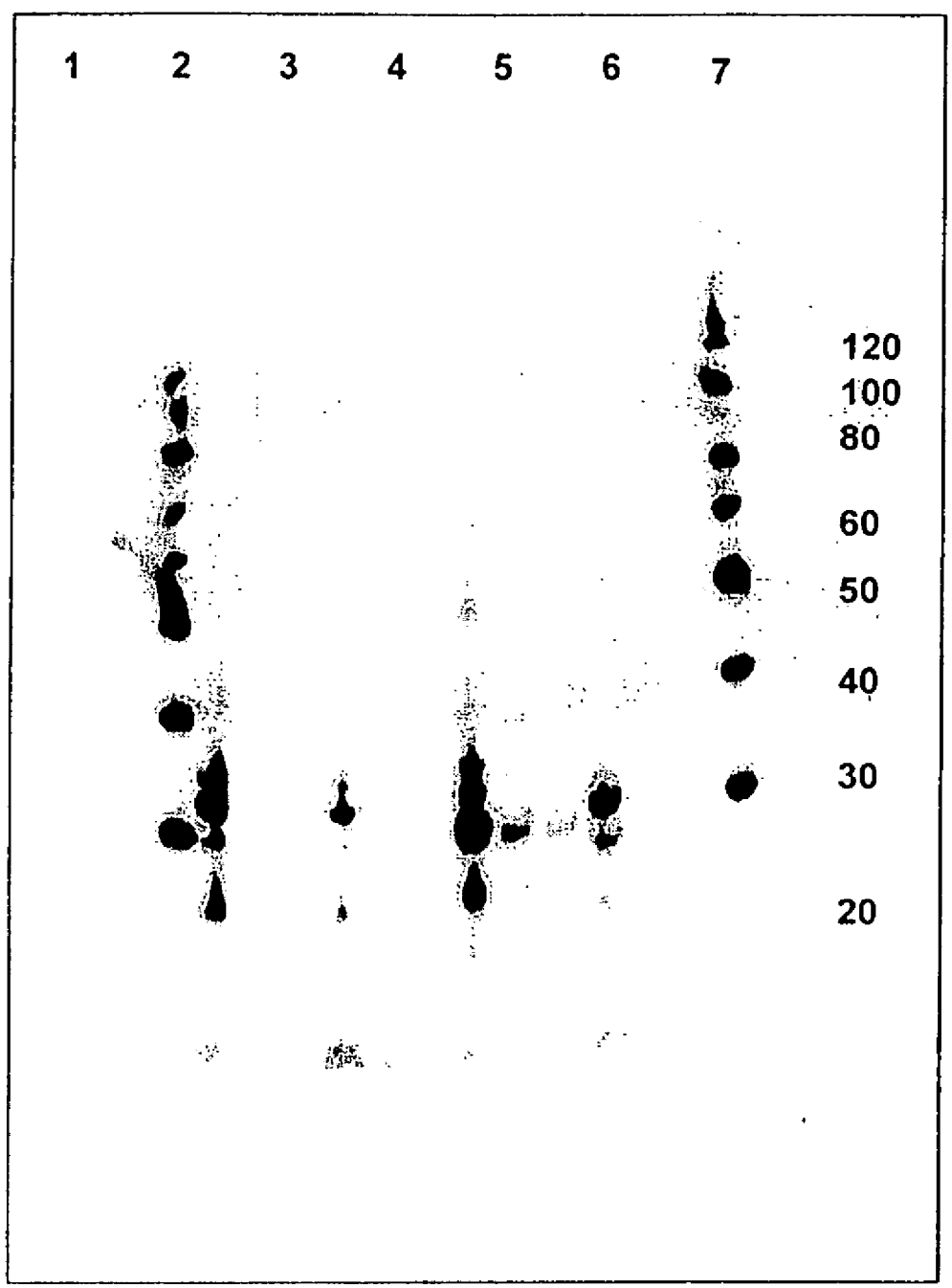
FIG. 1 shows a western blot of GM-CSF production from variant F07 (Var. 1) and wild-type. Samples were produced as described in the text. Lane 1 F07 total GM-CSF from cell lysate. Lane 2 F07 periprep with 4000 rpm spin. Lane 3 F07 periprep with 15000 rpm spin. Lane 4 Wild type total GM-CSF from cell lysate. Lane 5 Wild type periprep with 4000 rpm spin. Lane 6 Wild type periprep with 15000 rpm spin. Lane 7 Magic marker (Invitrogen).

The Sequence Listing is submitted as an ASCII text file, created on Jul. 9, 2010, 24.1 kB, which is incorporated by reference herein.

According to one aspect of the present invention there is provided a method of providing a subject polypeptide variant with improved stability compared with a parent subject polypeptide, the method comprising:

(a) providing mRNA molecules, each mRNA molecule comprising a nucleotide sequence encoding a subject polypeptide variant and lacking an in-frame stop codon;

(b) incubating the mRNA molecules under conditions for ribosome translation of the mRNA molecules to produce encoded subject polypeptide variants, whereby complexes each comprising at least mRNA and encoded subject polypeptide variant are formed;

(c) bringing the complexes into contact with a receptor, ligand or specific binding pair member that binds the parent subject polypeptide, and selecting one or more complexes each displaying a subject polypeptide variant able to bind the receptor, ligand or specific binding pair member under the conditions of the selection;

wherein one or more of steps (i), (ii) and (iii) are performed as follows:

(i) two or more stability selection pressures are applied simultaneously during translation in step (b);

(ii) two or more stability selection pressures are applied simultaneously during selecting in step (c);

(iii) at least one stability selection pressure is applied during translation in step (b) and continues to be applied during selecting in step (c), and at least one further stability selection pressure is applied during selecting in step (c); and (d) determining stability of selected subject polypeptide variant or variants, whereby one or more subject polypeptide variants with improved stability compared with the parent subject polypeptide are obtained.

Methods of the invention use selection or display technology incorporating in vitro translation and covalent or non-covalent linkage between genotype, such as RNA, and the encoded phenotype, such as polypeptide of interest to select for polypeptide variants that have improved stability compared with the parent polypeptide and that retain functionality.

Methods of the invention may use ribosome display technology or mRNA display technology, for example. In the case of ribosome display, complexes formed in a method of the invention will additionally comprise a ribosome.

A stability selection pressure may be selected from dithiothreitol (DTT), glutathione, Tris[2-carboxyethyl]phosphine hydrochloride (TCEP), mercaptoethanol, urea, guanidine hydrochloride (GuHCl), depletion of chaperons, pH, small molecule protein folding inhibitors, proteases, sodium thiocyanate, hydrophobic interaction chromatography (HIC) and temperature. (Application of increased temperature provides selection pressure for stability.)

A stability selection pressure during translation of variant polypeptides may be dithiothreitol (DTT), glutathione, Tris [2-carboxyethyl]phosphine hydrochloride (TCEP), mercaptoethanol, urea, guanidine hydrochloride (GuHCl), depletion of chaperons, pH and small molecule protein folding inhibitors. Optionally, a stability selection pressure may not be present during translation. Preferably, DTT is used as a selection pressure during translation.

At least two stability selection pressures may be used simultaneously for selecting polypeptide variants in methods of the invention. Two or more stability selection pressures may be selected from dithiothreitol (DTT), glutathione, Tris [2-carboxyethyl]phosphine hydrochloride (TCEP), mercaptoethanol, urea, guanidine hydrochloride (GuHCl), proteases, sodium thiocyanate, HIC and temperature. Preferably, selection pressures used simultaneously include HIC and temperature at the selection stage, preferably in a process comprising use of DTT at the translation stage. Temperature applied as a selection pressure may be room temperature, preferably about 25° C.

One or more of the stability selection pressures may be present during capture of selected variants able to bind a receptor, ligand or specific binding pair member that binds the parent subject polypeptide. Alternatively, one or more of the two selection pressures may be removed prior to capture of selected variants by the receptor, ligand or specific binding pair member. The presence or absence of a selection pressure may at least in part depend on whether a selection pressure may interact with or disrupt the interaction between selected variant and receptor, ligand or specific binding pair member. For example, where a protease is used as a selection pressure, this is preferably removed or inactivated before the receptor, ligand or specific binding pair member is introduced, to avoid degradation of the receptor, ligand or specific binding pair member by the protease.

In a method of the invention, stability may be determined by comparing ability of selected subject polypeptide variant or variants to bind receptor, ligand or specific binding pair member when displayed when produced in the presence and absence of a selection pressure, for example DTT.

A measure of stability employed in the context of the present invention can be expressed as a ratio of ability of a variant to bind receptor, ligand or specific binding pair member thereof in the presence of dithiothreitol (DTT), e.g. 10 mM DTT, as determined in a radioimmunoassay (RIA), and ability of the variant to bind the receptor, ligand or specific binding member pair in the absence of DTT in the same radioimmunoassay. The greater the value of the ratio, the greater the stability of the variant and hence its existence in folded state in a reducing environment.

Compared with a wild-type polypeptide, a variant may have such a ratio that is improved by about or at least about five-fold, more preferably about or at least about ten-fold, fifteen-fold, twenty-fold, twenty-five-fold or thirty-fold.

In a method of the invention stability may be determined by comparing aggregation of selected subject polypeptide variant or variants with that of the parent subject polypeptide.

Thus, another measure of stability that may be employed in the context of the present invention is to compare aggregation of a variant polypeptide over time with that of the wild-type polypeptide. For example, both wild-type and variant polypeptides may be stored at a range of temperatures (for example from 5° C. to 45° C.) and then analysed for breakdown products and aggregated material using routine methods known in the art. A stable protein better remains in folded state and is less prone to breakdown and aggregation.

Aggregation may be assessed by screening for expression of soluble protein, for example, comprising expression of a protein followed by centrifugation and analysis by PAGE and immunoblotting. Detection of individual bands that are not removed by centrifugation as opposed to a smear or bands that are removed after centrifugation indicates the presence of soluble protein rather than aggregates.

Stability of polypeptide variants may be assessed by determining the function or activity of a variant in a biological activity assay.

A variant polypeptide with improved stability may retain 90% residual activity at a temperature that is 2-10° C. higher than that at which wild-type protein retains 90% residual activity, e.g. 2, 3, 4, 5, 6, 7, 8, 9 or 10° C. higher. The percentage of residual (i.e. folded, active) protein may be measured by routine biochemical techniques such as HPLC, SDS PAGE or by activity assays such as binding assays or eliciting a response from cells.

A method of the invention may comprise retrieving mRNA from a selected complex. Thus, mRNA from a selected complex or complexes may be isolated and/or used in provision of DNA, which DNA may be used in production of the encoded specific binding pair member and/or employed in a further round of selection using ribosome display, mRNA display, or other systems such as bacteriophage display, yeast display.

Generally a library, population or repertoire of diverse mRNA sequences is provided, encoding a library, population or repertoire of diverse peptides or polypeptides with the potential to form subject polypeptides.

A ribosome translation system employed in a method of the invention may be prokaryotic or eukaryotic. Both are established in the art for display and selection of a number of different binding molecules. See for example: Mattheakis et al., (1994) PNAS USA 91, 9022-9026; Mattheakis et al., (1996) Methods Enzymol 267, 195-207; Gersuk et al., (1997) Biotech and Biophys Res Com 232, 578-582; Hanes and Pluckthun (1997) PNAS USA 94, 4937-4942; Hanes et al., (1998) PNAS USA 95, 14130-50; He and Taussig (1997) NAR 5132-5234. (Hanes et al. (2000) Meth. Enzymol. 328, 403-430, Plückthun et al. (2000) Adv. Prot. Chem 55, 367-403).

A construct for ribosome display may comprise a RNA polymerase promoter (e.g. T7 polymerase promoter), ribosome binding site, Kozak consensus sequence, initiation codon and coding sequence of polypeptide, peptide or protein. One or more nucleotide sequences encoding one or more detection tags may be included to provide for production of a polypeptide, peptide or protein further comprising one or more detection tags (e.g. histidine tag). One or more additional features may incorporated into a construct for use in ribosome display, e.g. as disclosed in WO01/75097.

An mRNA translation system used in a method of the invention may be any suitable available system. A prokaryotic or eukaryotic translation system may be used, for example crude E. coli or wheat (e.g. as supplied by Roche, Invitrogen) lysate, rabbit reticulocyte lysate (e.g as supplied by Ambion, Promega) or a reconstituted system such as PURE (reported by Shimizu et al., Cell-free translation reconstituted with purified components, Nat. Biotechnol. 19 (2001) 751-755.)

In some embodiments of the present invention, mRNA molecules for incubation in the translation system are provided by means of RT-PCR reactions in which at least one of the RT-PCR primers is a mutagenic primer encoding a diversity of different sequences for inclusion in a defined region of the mRNA coding region. For example, a defined region may be one encoding a CDR of an antibody molecule, preferably CDR3 of an antibody VH domain.

A defined region for mutation may comprise a residue found necessary for overall protein stability (Proba et al., (1998) J. Mol. Biol. 2 75, 245-253) or be an area of a protein which is likely to be involved in early aggregation events, such as exposed loops.

As described herein, methods of the invention are applicable to any protein capable of being produced in an in vitro system.

In preferred embodiments, the subject polypeptides for display are antibody molecules, usually single chain antibody molecules, such as scFv antibody molecules, VH, Fd (consisting of the VH and CH1 domains), or dAb molecules.

In other preferred embodiments, non-antibody subject polypeptides are employed, and these may include receptors, enzymes, peptides and protein ligands.

Examples of subject polypeptides include but are not limited to members of the family of four anti-parallel α-helix bundle proteins, such as interferons or interleukins, as well as the extra-cellular domain of complex receptors, such as tumour necrosis factor receptor II (TNFRII).

In a method according to the invention mRNA retrieved from a selected complex displaying a selected subject polypeptide variant may be amplified and copied into DNA encoding the selected subject polypeptide variant.

DNA may be provided in an expression system for production of a product, which product is the selected subject polypeptide variant or a polypeptide chain of the selected subject polypeptide variant. DNA encoding the selected subject polypeptide variant or a polypeptide chain of the selected subject polypeptide variant may be provided within a nucleotide sequence to provide a nucleotide sequence encoding a fusion protein comprising the selected subject polypeptide variant, or a polypeptide chain of the selected subject polypeptide variant, fused to additional amino acids. DNA comprising said nucleotide sequence encoding said fusion protein may be provided in an expression system for production of a product, which product is the fusion protein. Methods of the invention may further comprise isolating or purifying the product, which may be formulated into a composition comprising at least one additional component.

Following selection and retrieval of nucleic acid encoding the displayed subject polypeptide variant, the nucleic acid may be used in provision of the encoded subject polypeptide or may be used in provision of further nucleic acid (e.g. by means of an amplification reaction such as PCR). Selected mRNA may be subject of RT-PCR to generate cDNA copies. Nucleic acid encoding component parts of a subject polypeptide variant may be used in provision of further molecules, for instance reformatted antibody molecules, fusion proteins, immunoadhesins and so on. Thus, for example, nucleic acid encoding the VH and VL domains of a selected scFv antibody molecule may be used in construction of sequences encoding antibody molecules of other formats such as Fab molecules or whole antibody.

In a method of the invention DNA encoding the selected subject polypeptide variant or a polypeptide chain of the selected subject polypeptide variant may be mutated to encode a polypeptide that comprises an amino acid sequence that differs from the selected subject polypeptide variant or polypeptide chain of the selected subject polypeptide variant. Mutated DNA encoding said polypeptide may be provided in an expression system for production of a product, which product is said polypeptide. A method may further comprise isolating or purifying the product, optionally formulating the product into a composition comprising at least one additional component.

Furthermore, nucleic acid may be subject to any technique available in the art for alteration or mutation of its sequence. This may be used to provide a derivative sequence. A sequence may be provided which encodes a derivative of the selected subject polypeptide variant or component thereof, for example a derivative that comprises an amino acid sequence that differs from the selected subject polypeptide variant or component thereof by addition, deletion, insertion and/or substitution of one or more amino acid sequences. A method providing such a derivative may provide a fusion protein or conjugate wherein an additional peptide or polypeptide moiety is joined to the subject polypeptide variant or component thereof, e.g. a toxin or label.

Encoding nucleic acid, whether reformatted or not, may be used in production of the encoded polypeptide or peptide using any technique available in the art for provision of polypeptides and peptides by recombinant expression.

Further aspects and embodiments of the present invention are disclosed herein in and preferred aspects and embodiments are subject to the claims included below.

The present invention is illustrated by methods wherein the parent subject polypeptide is a wild-type erythropoietin (EPO). In particular, the parent subject polypeptide is human wild-type EPO having the amino acid sequence shown in SEQ ID NO: 2.

Methods described herein provide a subject polypeptide variant comprising a set of mutations in the human wild-type sequence of SEQ ID NO: 2 selected from the group consisting of the following sets of mutations:

```
                                           (SEQ ID NO: 10)
    (1)   L16I I25F T27M V61A R139H T157V (SEQ ID NO: 11)
    (2)   D8V T26A T27A S126P G158E (SEQ ID NO: 12)
    (3)   D8V T27A Y49N W64R V82A E89G 126P G158E (SEQ ID NO: 13)
    (4)   T26A W64R A135V G158E (SEQ ID NO: 14)
    (5)   D8V V74F T107A N147D.
```

Further, the present invention is illustrated by methods wherein the parent subject polypeptide is a wild-type granulocyte-macrophage colony stimulating factor (GM-CSF). In particular, the parent subject polypeptide is human wild-type GM-CSF having the amino acid sequence shown in SEQ ID NO: 4.

Methods described herein provide a subject polypeptide variant comprising a set of mutations R4S H15L A18V I43V K63T T102A (SEQ ID NO: 15) in the human wild-type sequence of SEQ ID NO: 4.

Furthermore, the present invention is illustrated by methods wherein the parent subject polypeptide is a wild-type granulocyte colony stimulating factor (G-CSF). In particular, the parent subject polypeptide may be human wild-type G-CSF having the amino acid sequence shown in SEQ ID NO: 6.

Methods described herein provide a subject polypeptide variant comprising a set of mutations C17G W58R Q70R F83L (SEQ ID NO: 16) in the human wild-type sequence of SEQ ID NO: 6.

In general, within aspects and embodiments of the present invention, the parent polypeptide comprises a folded protein domain and most preferably has a biological activity. Biological activity may include ability to bind to a cognate binding partner, such as a receptor or ligand, and may include ability to trigger a receptor activity or biological response, ability to catalyse a reaction and so on.

As described herein, a measure of stability employed in the context of the present invention can be expressed as a ratio of the ability of a subject polypeptide variant to bind a cognate receptor, ligand or other specific binding pair member following production by translation from encoding mRNA in the presence of dithiothreitol (DTT) or any other stability selection pressure, for example, increased temperature or application of HIC matrix as determined in a radio immunoassay (RIA), and ability of the subject polypeptide variant to bind the subject polypeptide receptor, ligand or other specific binding pair member following production by translation from encoding mRNA in the absence of any selection pressure in the same radio immunoassay. The translation may be carried out in the presence of $^{35}$S-Met so that radioactively labelled protein is generated. Non-specific binding or background binding may be determined by applying the translation mix to either a non-cognate receptor and/or an irrelevant antigen such as BSA and measuring the residual radioactivity on these surfaces.

A measure of stability of a selected subject polypeptide variant, for example an EPO variant, employed in the context of the present invention may be expressed as a ratio of ability of a variant, for example an EPO variant, to bind receptor, ligand or specific binding pair member thereof, for example, EPO receptor for an EPO variant, in the presence of dithiothreitol (DTT), e.g. 10 mM DTT, as determined in a radioimmunoassay (RIA), and ability of the variant, for example an EPO variant, to bind the receptor, ligand or specific binding pair member, for example EPO receptor for an EPO variant, in the absence of DTT in the same radioimmunoassay. The greater the value of the ratio, the greater the stability of the variant, for example, EPO variant, and hence its existence in folded state in a reducing environment.

Compared with wild-type EPO, an EPO variant may have such a ratio that is improved by about or at least about five-fold, more preferably about or at least about ten-fold, fifteen-fold, twenty-fold, twenty-five-fold or thirty-fold.

Provision of variants with improved stability and retained functionality is demonstrated in the experiments described below. See for instance Table 1, which provides measured ratios of EPO receptor binding in the presence and absence of DTT for wild-type EPO (0.00) and various EPO variants (ranging from 0.1 to 0.33).

Also as described herein, a measure of stability employed in the context of the present invention can be aggregation. Thus, stability may be determined by comparing aggregation of an EPO variant over time with that of wild type EPO. For example, both wild type EPO and variant EPO can be stored at a range of temperatures (for example from 5° C. to 45° C.) and then analysed for breakdown products and aggregated material using routine methods known in the art. A stable protein better remains in folded state and is less prone to breakdown and aggregation.

An EPO variant polypeptide with improved stability may retain 90% residual activity at a temperature that is 2-10° C. higher at which wild-type protein retains 90% residual activity, e.g. 2, 3, 4, 5, 6, 7, 8, 9 or 10° C. higher. The percentage of residual (i.e. folded, active) protein may be measured by routine biochemical techniques such as HPLC, SDS PAGE or by activity assays such as binding assays or eliciting a response from cells.

For example, aggregation may be assessed by screening for expression of soluble protein, for example, comprising expressing a protein followed by analysis by PAGE and immunoblotting. Detection of individual bands by immunoblotting as opposed to a smear indicates the presence of soluble protein rather than protein aggregates.

GM-CSF variants that had improved expression profiles were identified by methods of the invention. Products from GM-CSF variants were detected as primarily a single band, compared to a laddered smear of wild-type product. Products from G-CSF variants were also detected as a single band.

Stability of polypeptide variants may be assessed by determining the function or activity of a variant in a biological activity assay.

For example, stability of GM-CSF variants may be assessed in a TF1 cell proliferation assay and stability of G-CSF variants may be assessed in a OCI/AML5 cell proliferation assay. The nature of a biological assay used to determine stability of course depends on the function or activity of the subject polypeptide. Suitable methods for assaying particular protein activities are known in the art.

Provision of variants with improved stability and retained functionality is demonstrated in the experiments described below. See for instance Table 2, which provides results of TF1 proliferation assays for a GM-CSF variant compared to wild-type GM-CSF and Table 3, which provides results of OCI/AML5 cell proliferation assays for a G-CSF variant compared to wild-type G-CSF.

A subject polypeptide variant according to the present invention may be provided to contain one or more additional changes compared with a starting or parent polypeptide, which may be a wild-type or natural protein or a previously obtained polypeptide variant. A number of different modifications to subject polypeptides are known (both naturally occurring mutants and artificially created variants) with modified properties compared with wild-type. One or more of these properties may be retained or provided in a subject polypeptide variant according to the present invention.

Following provision in accordance with a method of the invention, a subject polypeptide variant may be isolated and/or purified (e.g. using an antibody) for instance after production by expression from encoding nucleic acid (for which see below). Thus, a polypeptide may be provided free or substantially free from contaminants. A polypeptide may be provided free or substantially free of other polypeptides. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A convenient way of producing a polypeptide according to the present invention is to express nucleic acid encoding it, by use of the nucleic acid in an expression system. Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Nucleic acid encoding a subject polypeptide variant may be provided in accordance with methods of the invention.

Generally, nucleic acid according to the present invention is provided as an isolate, in isolated and/or purified form, or free or substantially free of contaminants. Nucleic acid may be wholly or partially synthetic and may include genomic DNA, cDNA or RNA.

Nucleic acid may be provided as part of a replicable vector, and also provided by the present invention are a vector including nucleic acid encoding a subject polypeptide variant of the invention, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as *E. coli*.

A host cell may be provided containing nucleic acid as disclosed herein. The nucleic acid may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

The nucleic acid may be introduced into a host cell. The introduction, which may (particularly for in vitro introduction) be generally referred to without limitation as "transformation" or "transfection", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Following production of a subject polypeptide variant by expression, its activity, e.g. ability to bind subject polypeptide receptor or ligand or other specific binding pair member, can be tested routinely.

According to a further aspect of the present invention there is provided a method of making a subject polypeptide variant with improved stability compared with a parent subject polypeptide, the method comprising:

producing a subject polypeptide variant by expression from encoding nucleic acid, wherein production is by translation in the presence and absence of DTT, and the production is in a ribosome display system such that ribosome complexes each comprising a subject polypeptide variant and mRNA encoding the subject polypeptide variant are produced;

testing the subject polypeptide variant comprised in ribosome complexes for improved stability compared with parent subject polypeptide, for example using as a measure of stability the ratio of binding activity to subject polypeptide receptor, ligand or specific binding pair member when translated in the presence of DTT in a radioimmunoassay and of binding activity to subject polypeptide receptor, ligand or specific binding pair member when translated in the absence of DTT in the same assay, wherein ability to bind is assessed in the presence of hydrophobic interaction chromatography which is performed at room temperature.

The ratio may be improved by about or at least about five-fold or more as indicated elsewhere herein.

A method of the invention may comprise a method of making a subject polypeptide variant polypeptide that has improved stability compared with a parent subject polypeptide, the method comprising:

producing a subject polypeptide variant in a ribosome display system by expression from encoding nucleic acid in the presence and absence of DTT;

testing for improved stability by comparison of binding of the subject polypeptide variant to cognate receptor, ligand or specific binding pair member when displayed on ribosomes and produced in the presence and absence of DTT, using hydrophobic interaction chromatography at room temperature.

A method of the invention may comprise the step of isolating the subject polypeptide variant prior to the testing and/or mutating nucleic acid encoding a parent subject polypeptide, to provide a nucleic acid encoding a subject polypeptide variant prior to expression therefrom.

Such a method may optionally include isolating and/or purifying the subject polypeptide variant following its production and prior to testing.

Someone performing the method may additionally perform a prior step of providing a subject polypeptide variant by altering the amino acid sequence of the subject polypeptide variant, e.g. by substitution and/or insertion of one or more amino acids as discussed. Various different variants may be provided and tested for the desired activity, e.g. in order to identify from a range of variants one or more variants with the properties desired in accordance with the present invention. Normally, alteration of the amino acid sequence of subject polypeptide will be made by altering the coding sequence of nucleic acid encoding subject polypeptide. One or more nucleotides may be altered to alter one or more codons and thus the encoded amino acid(s). As mentioned elsewhere herein, and will be apparent to those skilled in the art, any suitable technique for mutagenesis, especially directed or site-specific mutagenesis, can be employed in order to change the coding sequence, and thus the encoded amino acid sequence, for a subject polypeptide variant. Reviewed by McPherson and Moller (2000) PCR. The Basics from Background to Bench; BIOS Scientific Publishers Ltd.

Selection of a subject polypeptide variant with improved stability in accordance with the present invention may employ ribosome display, translation in the ribosome display system in the presence and absence of DTT, and selection of subject polypeptide variants in complex with ribosomes and mRNA using HIC at room temperature.

A further aspect of the present invention provides a method of providing, identifying or obtaining a subject polypeptide variant which has improved stability compared with parent subject polypeptide, the method comprising:

mutating nucleic acid encoding an parent subject polypeptide to provide one or more nucleic acids with sequences encoding one or more subject polypeptide variants with altered amino acid sequences ("subject polypeptide variants");

expressing the nucleic acid or nucleic acids as mRNA in a ribosome display system to produce the encoded subject polypeptide variant or variants by translation from the mRNA, wherein the translation is performed in the presence of DTT and in the absence of DTT;

selecting for a subject polypeptide variant or variants thus produced for improved stability compared with parent subject polypeptide by hydrophobic interaction chromatography;

wherein the hydrophobic interaction chromatography is performed at room temperature.

By room temperature is meant any temperature at or above 20° C. and at or below 30° C., preferably of about 25° C.

A library or diverse population of variants may be produced and tested for the desired abilities.

Mutation may be at any residue identified within a set of mutations as disclosed herein, any cysteine and/or any residue at which N-glycosylation occurs or in any other way as described herein.

The subject polypeptide that is subject to the mutation may be a wild-type polypeptide or an existing variant, e.g. a variant previously selected on the basis of a desired property, e.g. improved or increased stability.

One or more subject polypeptide variants with the desired properties may be identified or selected.

After a subject polypeptide variant of the invention has been identified or obtained it may be provided in isolated and/or purified form, it may be used as desired, and it may be formulated into a composition comprising at least one additional component, such as a pharmaceutically acceptable excipient or carrier. Nucleic acid encoding the subject polypeptide variant may be used to produce the variant for subsequent use. As noted, such nucleic acid may, for example, be isolated from a library or diverse population initially provided and from which the subject polypeptide variant was produced and identified.

A subject polypeptide variant in accordance with the present invention may be used in methods of diagnosis or treatment of the human or animal body of subjects, preferably human.

Accordingly, further aspects of the invention provide methods of treatment comprising administration of a subject polypeptide variant as provided, pharmaceutical compositions comprising such a subject polypeptide variant, and use of such a subject polypeptide variant in the manufacture of a medicament for administration, for example in a method of making a medicament or pharmaceutical composition comprising formulating the subject polypeptide variant with a pharmaceutically acceptable excipient.

Clinical indications in which a subject polypeptide variant may be used are those in which the subject polypeptide provides therapeutic benefit.

In accordance with the present invention a subject polypeptide variant may be given to an individual, preferably by administration in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be any suitable route, but most likely injection, especially intravenous injection.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Further aspects and embodiments of the present invention will be apparent to those skilled in the art in the light of the present disclosure, including the following experimental exemplification.

All documents mentioned anywhere in this specification are incorporated by reference.

EXPERIMENTAL EXAMPLES

Example 1

Construction of Library of EPO Variants and Selection of EPO Variants for Improved Stability Library Construction.

EPO cDNA was obtained from Invitrogen. The mature sequence was reformatted into the ribosome display linear template which was subsequently used for library creation. At the DNA level, a T7 promoter was added at the 5'-end for efficient transcription to mRNA. At the mRNA level, the construct contained a prokaryotic ribosome-binding site (Shine-Dalgarno sequence). At the 3' end, a portion of gIII was added to act as a spacer (Hanes et al., (2000) Meth Enzymol 328:.404). A library of variants was created using error prone PCR, following the manufacturer's protocol (BD Bioscience), with an error rate of 8.1 nucleotide mutations/molecule. This introduced 4 mutations per molecule and a library of approximately $2.5 \times 10^{10}$ variant molecules.

Selections for Stability.

Selections were performed with at least two simultaneous stability selection pressures including; DTT, HIC and increased temperature, followed by selection for functional activity.

The reducing agent dithiotheritol (DTT) was present during the translation and selection. DTT prevents disulphide bridge formation, which is an important component of EPO stability. Following translation, the translation mix with DTT was incubated with hydrophobic interaction chromatography (HIC) matrix at 25° C. The combination of DTT, HIC and increased temperature of 25° C. compared with the usual 4° C. should capture and remove the less stable variants that have unfolded and or mis-folded due to the selection pressure. HIC matrix is removed from the mix for example by centrifugation or filtration. A buffer exchange step may also be required before progressing to the functional selection.

In vitro translations and selections were performed in the presence and absence of DTT as described in Jermutus et al., (2001), with the following exceptions:
1. Translations were carried out at 30° C. for 10 minutes.
2. HIC and increased temperature were used as added selection pressures. Following translation with and without DTT the translation was stopped in buffer containing KCl (1 M increasing to 3 M) and DTT at the same concentration as the translation. The translation mix was then incubated with 1 ml bed volume of HIC beads (butyl-, octyl- and phenyl-sepharose, Amersham). After shaking for 30 minutes at 25° C. the HIC beads were removed by centrifugation at room temperature.
3. The supernatant was then cooled to 4° C. and functional selections were performed whereby, following incubation of the stability selected library with EPO receptor fusion protein, the fusion protein was captured and the bound complexes were recovered by magnetic separation whilst unbound complexes were washed away. The mRNA encoding the bound EPO variants was then recovered by RT-PCR and the selection process was repeated. Four rounds of selection were performed with more destabilising combinations of DTT, HIC and increased temperature.

The PCR products from round 4 were cloned into the in vitro expression vector pIVEX2.3d (Roche). In brief the outputs were PCR amplified to introduce a 5' Nco1 restriction site and at the 3' end a stop codon followed immediately by a Not1 restriction site. The stop codon allowed the expression of untagged variant EPO. The product was gel purified, double digested with Not1 and Nco1 (New England Biolabs) and gel purified. The digested product was ligated into Not1 Nco1 digested pIVEX2.3d and transformed into *E. coli* TG1 cells. Individual colonies were picked into 96 well plates for screening and sequencing.

Example 2

Screening of Single EPO Variants in Primary Stability RIA

EPO variants were screened for stability using the primary stability RIA (radio immunoassay) as described in Jermutus et al., (2001). In brief for each variant a linear DNA template was amplified, transcribed, the mRNA purified on G25 sephadex columns and quantified. For each variant in vitro translations in the presence of $^{35}$S-labelled methionine were set up in duplicate at 30° C. for 30 minutes, one in non-reducing conditions and one in 10 mM DTT (dithiothreitol). The translations were stopped with PBS with 0.05% Tween 20, with DTT at the same concentration as the translations. The translation mixture was incubated on a plate coated with EPO receptor for 1 hour at room temperature. Plates were washed three times in PBS with 0.05% Tween 20 and three times in PBS.

The remaining radioactivity was eluted with 0.1 M triethylamine and quantified by liquid scintillation counting. A measure of the variants' stability was calculated by dividing the RIA signal in 10 mM DTT by the RIA signal in the absence of DTT. The more stable the variant the bigger the ratio i.e. if inactive in DTT the ratio=0, if fully active in DTT the ratio=1.

Forty eight cloned EPO variants from round 4 were screened as described above. From this 5 EPO variants were identified that were more stable than WT (Table 1).

TABLE 1

Results of stability RIA for 5 variants with absolute RIA signal after non-reducing conditions (DTT−) and measure of stability calculated as described in the text (DTT+/DTT−).

| Clone  | DTT−  | DTT+/DTT− |
|--------|-------|-----------|
| WT EPO | 5009  | 0.00      |
| Var 1  | 67552 | 0.33      |
| Var 2  | 4890  | 0.14      |
| Var 3  | 13553 | 0.12      |
| Var 4  | 40087 | 0.1       |
| Var 5  | 14895 | 0.1       |

Sequence Analysis of EPO Variants

The EPO variants from round 4 were sequenced, the sequence of the 5 more stable variants is described below as differences at the amino acid level from WT EPO having the amino acid sequence shown as SEQ ID NO: 2.

```
                                              (SEQ ID NO: 10)
Var 1  L16I I25F T27M V61A R139H T157V (SEQ ID NO: 11)
Var 2  D8V T26A T27A S126P G158E (SEQ ID NO: 12)
Var 3  D8V T27A Y49N W64R V82A E89G S126P G158E (SEQ ID NO: 13)
Var 4  T26A W64R A135V G158E (SEQ ID NO: 14)
Var 5  D8V V74F T107A N147D
```

Example 3

Construction of a Library of GM-CSF Variants and Selection for Stability to Improve Expression Library Construction.

Human GM-CSF cDNA was cloned, and the mature sequence reformatted into the ribosome display linear template that was subsequently used for library creation. At the DNA level, a T7 promoter was added at the 5'-end for efficient transcription to mRNA. At the mRNA level, the construct contained a prokaryotic ribosome-binding site (Shine-Dalgarno sequence). At the 3' end a portion of gIII was added to act as a spacer (Hanes et al., (2000) Meth Enzymol 328:.404). A library of variants was created using error prone PCR, following the manufacturer's protocol (BD Bioscience), with an error rate of 8.1 nucleotide mutations/molecule. This introduced 3 mutations per molecule.

Selections for Stability.

Selections were performed as in Example 1 with at least two simultaneous stability selection pressures including; DTT, HIC and increased temperature, followed by selection for functional activity by binding to GM-CSF receptor fusion protein. Four rounds of selection were performed with increasingly destabilising combinations of DTT, HIC and increased temperature.

The PCR product from round 4 was cloned into the periplasmic expression vector pcantab6. (McCafferty et al., Appl Biochem Biotechnol. (May-June 1994) 47(2-3):157-71; discussion 171-3). In brief the outputs were PCR amplified to introduce a 5' Nco1 restriction site and at the 3' end a Not1 restriction site. The product was gel purified, double digested with Not1 and Nco1 (New England Biolabs) and gel purified. The digested product was ligated into Not1 Nco1 digested pcantab6 and transformed into E. coli HB2151 (Biostat Diagnostics). Individual colonies were picked into 96 well plates for screening and sequencing.

Example 4

Screening of Single GM-CSF Variants in Primary Expression Screen

GM-CSF variants were screened for soluble expression using 96 well expression, PAGE and immunoblotting. In brief, soluble expression was achieved using Overnight Express™ Autoinduction System (Merck Bioscience) and the product run on E-PAGE protein electrophoresis system (Invitrogen). For periplasmic extraction cells were harvested by centrifugation. The periplasmic material released by osmotic shock, debris removed by centrifugation and leaving expressed protein in supernatants. Samples of the extracted proteins were run using E-PAGE (Invitrogen) SDS-PAGE system allowing 96 samples to run simultaneously. Then gel was blotted onto PVDF membrane and subsequently probed with a polyclonal anti-human GM-CSF antibody (Chemicon) and detected with anti-rabbit IgG HRP conjugate (Dako UK), ECL Plus chemiluminescent reagent (Amersham) and image capture using a Lumi Imager (Boehringer Mannheim).

Eighty-eight GM-CSF variants from round 4 were screened as described above. From this, GM-CSF variants were identified that had improved expression profiles. The products from these variants was primarily a single band, detected with anti GM-CSF antibody, compared to a laddered smear of wild type product.

Example 5

Soluble Expression of GM-CSF Variant

The periplasmic production of a GM-CSF variant and wild-type were compared in duplicate. The expression of recombinant protein from pCANTAB6 in E. coli HB2151 (Biostat Diagnostics) was achieved using the Overnight Express™ Autoinduction System (Merck Bioscience) in 50 ml volume in 250 ml Erlenmeyer flask. The final culture density was measured by absorbance of 1 in 10 dilution of culture at 600 nm wavelength (OD$_{600}$). All cultures were normalised to OD$_{600}$ of 1.0. The cells were harvested by centrifugation, the periplasmic material was released by osmotic shock (using 200 mM Tris [pH 8.0 at 4° C.], 1 mM EDTA, 0.5M Sucrose) and debris removed by low speed centrifugation at 4000 rpm using a microfuge. Insoluble protein was removed from the periplasmic extract by a high-speed centrifugation at 15000 rpm in a mcirofuge. The samples were run on NuPAGE Bis-Tris gel system (Invitrogen) in 1×MES buffer. The gel was blotted onto PVDF membrane and subsequently probed with a polyclonal anti-human GM-CSF antibody (Chemicon) and detected with anti-rabbit IgG HRP conjugate (Dako UK), ECL Plus chemiluminescent reagent (Amersham) and image capture using a Lumi Imager (Boehringer Mannheim).

The GM-CSF variant Var. 1 (F07) produced soluble protein in the periplasm as shown in FIG. 1. The GM-CSF wild type produced no soluble protein (FIG. 1), as expected (Lundell et al., 1990).

The biological activity of variant and wild-type was assessed in a TF-1 cell proliferation assay. TF-1 cells were obtained from R&D Systems and maintained according to supplied protocols. Assay media comprised RPMI-1640 with GLUTAMAX I containing 5% foetal bovine serum and 1% sodium pyruvate. Prior to each assay, TF-1 cells were pelleted by centrifugation at 300×g for 5 mins, the media removed by aspiration and the cells resuspended in assay media. This process was repeated three additional times with cells resuspended at a final concentration of 1×105/ml in assay media. GM-CSF variants (in duplicate) were diluted to the desired concentrations in assay media. 100 µl of resuspended cells were then added to each assay point to give a total assay volume of 200 µl/well. Assay plates were incubated at 37° C. was for 72 hours at 37° C. under 5% CO2. 20 µl of tritiated thymidine (5 µCi/ml, NEN) was then added to each assay point and assay plates were returned to the incubator for a further 4 hours. Cells were harvested on glass fibre filter plates (Perkin Elmer) using a cell harvester. Thymidine incorporation was determined using a Packard TopCount microplate liquid scintillation counter. Data were analysed using Graphpad Prism software.

GM-CSF Var. 1 was more active than wild type GM-CSF in the TF1 proliferation assay (Table 2):

TABLE 2

$EC_{50}$ of GM-CSF wild type (WT) and variant Var. 1 in TF1 proliferation assay.

| Sample | $EC_{50}$ (nM) |
|---|---|
| WT | 1.179 |
| Var. 1 | 0.032 |

Sequence Analysis of GM-CSF Variant

Figure 2:
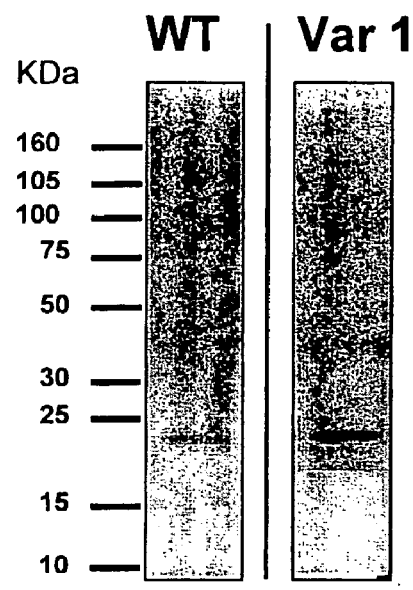
FIG. 2 shows a silver stained gel of G-CSF production from wild-type (WT) and variant (Var 1). The distinct band at approximately 25 kDa in the lane for Var 1 is monomeric G-CSF. Samples were produced as described in Examples 6 and 7.

The variant Var. 1 was sequenced. The sequence of the variant is described below as differences at the amino acid level from WT GM-CSF having the amino acid sequence shown in SEQ ID NO: 4.

```
                                        (SEQ ID NO: 15)
Var. 1     R4S H15L A18V I43V K63T T102A
```

Example 6

Construction of a Library of G-CSF Variants and Selection for Stability to Improve Expression Library Construction Human G-CSF cDNA was cloned, and mature sequences reformatted into the ribosome display linear template that was subsequently used for library creation. On the DNA level, a T7 promoter was added at the 5'-end for efficient transcription to mRNA. On the mRNA level, the construct contained a prokaryotic ribosome-binding site (Shine-Dalgarno sequence). At the 3' end a portion of gIII was added to act as a spacer (Hanes et al. 2000 Meth Enzymol 328:.404). A library of variants was created using error prone PCR, following the manufacturer's protocol (BD Bioscience), with an error rate of 8.1 nucleotide mutations/molecule. This introduced 3 mutations per molecule.

Selections for Stability

Selections were performed as in Example 1 with at least two simultaneous stability selection pressures including, DTT, temperature and HIC, followed by selection for functional activity by binding to biotinylated G-CSF receptor (RnD Cat No 381-ER-05). Four rounds of selection were performed with increasingly destabilising combinations of DTT, HIC and temperature.

The PCR product from round 4 was cloned into the periplasmic expression vector pcantab6. (McCafferty et al. Appl Biochem Biotechnol. 1994 May-June 47(2-3):157-71; discussion 171-3). In brief the outputs were PCR amplified to introduce a 5' Nco1 restriction site and at the 3' end a Not1 restriction site. The product was gel purified, double digested with Not1 and Nco1 (New England Biolabs) and gel purified. The digested product was ligated into Not1 Nco1 digested pcantab6 and transformed into *E. coli* HB2151 (Biostat Diagnostics). Individual colonies were picked into 96 well plates for screening and sequencing.

Example 7

Screening G-CSF Variants in Primary Expression Screen

G-CSF variants were tested for soluble expression in 96 well small scale expression screen. In brief, G-CSF variant proteins were expressed using the pCANTAB6 expression vector and *E coli* HB2151 cells (Biostat Diagnostics). The expression screen was performed in triplicate in 96-well master blocks (Greiner Bio-One), which contained 500 ml of 2×TY broth, 0.2% glucose, 100 mM ampicillin in each well. Each well was inoculated with lml of G-CSF variant glycerol stock, except the wells in column 12, which were inoculated with lml of wild-type G-CSF glycerol stock. The plates were incubated at 37° C./600 rpm for 6 hours in a HiGro incubator (Genemachines, Inc). IPTG was then added to each well to a final concentration of 1 mM and the plates were incubated overnight at 37° C./600 rpm. The cells were harvested by centrifugation at 2500×g for 10 minutes. The periplasmic material was released by resuspending each pellet in 200 ml of 200 mM Tris pH 8.0, 1 mM EDTA, 0.5M sucrose, 0.1% Tween at 4° C. and incubating on ice for 20 minutes. The cell debris was removed by centrifugation at 2500×g for 10 minutes. The three samples for each clone were pooled and 1400 ml were loaded onto 20 ml NiNTA PhyNexus tips (PhyNexus, Inc). The tips were washed with 340 ml of 50 mM Tris pH 7.4, 300 mM NaCl, 0.1% Tween followed by 100 ml of 50 mM Tris pH 7.4, 300 mM NaCl, 0.1% Tween, 30 mM Imidazole. They were then washed with 170 ml of 50 mM Tris pH 7.4, 300 mM NaCl, 0.1% Tween before the bound G-CSF was eluted using 100 mM HEPES pH 3.0, 140 mM NaCl, 0.2% Tween. The eluted samples were neutralised with 25 ml of 200 mM HEPES pH 8.0. The samples were run on 12% NuPAGE Bis-Tris gels (Invitrogen) in 1×MES buffer and the gels were stained using the SilverXpress silver staining kit (Invitrogen).

Eighty-eight G-CSF variants from round 4 were screened as described above. From this, a G-CSF variant with an improved expression profile was identified. The product from this variant was primarily a single band detected with silver staining, compared to virtually undetectable wild-type production (FIG. 2).

Example 8

Large-Scale Expression and Purification of G-CSF Variants

The large-scale periplasmic production of a G-CSF variant and wild-type G-CSF were compared. A single colony of each G-CSF was used to inoculate 400 ml of 2×TY broth, 0.2% glucose, 100 mM ampicillin, in a 2 L conical flask. The cultures were incubated at 37° C./300 rpm for 6 hours before IPTG was added to a final concentration of 1 mM. The cultures were incubated overnight at 37° C./300 rpm. The cells were harvested by centrifugation at 16800×g for 10 minutes. The periplasmic material was released by resuspending each pellet in 25 ml of 200 mM Tris pH 8.0, 1 mM EDTA, 0.5M sucrose, 0.1% Tween at 4° C. and incubating on ice for 20 minutes. The cell debris was removed by centrifugation at 12000×g for 10 minutes. The purifications were performed using an ÄKTA Explorer (GE Healthcare). For each purification, the periplasmic sample was passed over a 5 ml HisTrap HP column (GE Healthcare) that had been equilibrated in 50 mM Tris pH 8.0, 300 mM NaCl, 0.1% Tween. The column was washed with 50 ml of 50 mM Tris pH 8.0, 300 mM NaCl, 0.1% Tween, 30 mM Imidazole before the bound G-CSF was eluted using 50 mM Tris pH 8.0, 300 mM NaCl, 0.1% Tween, 200 mM Imidazole. The eluted sample was then run down a Superdex 75 16/30 gel filtration column (GE Healthcare) that had been equilibrated in 2×PBS, 0.1% Tween.

Figure 3:
FIG. 3 shows SEC traces and yields from 50 ml periplasmic expression for wild-type (WT) and variant (Var 1). Samples were produced as described in Example 8. For Var 1, arrow (1) indicates aggregate G-CSF and arrow (2) indicates monomer G-CSF. For monomer G-CSF (arrow (2)), the lower peak is measured at O.D 254 and the upper peak at O.D 280.
Figure 3:
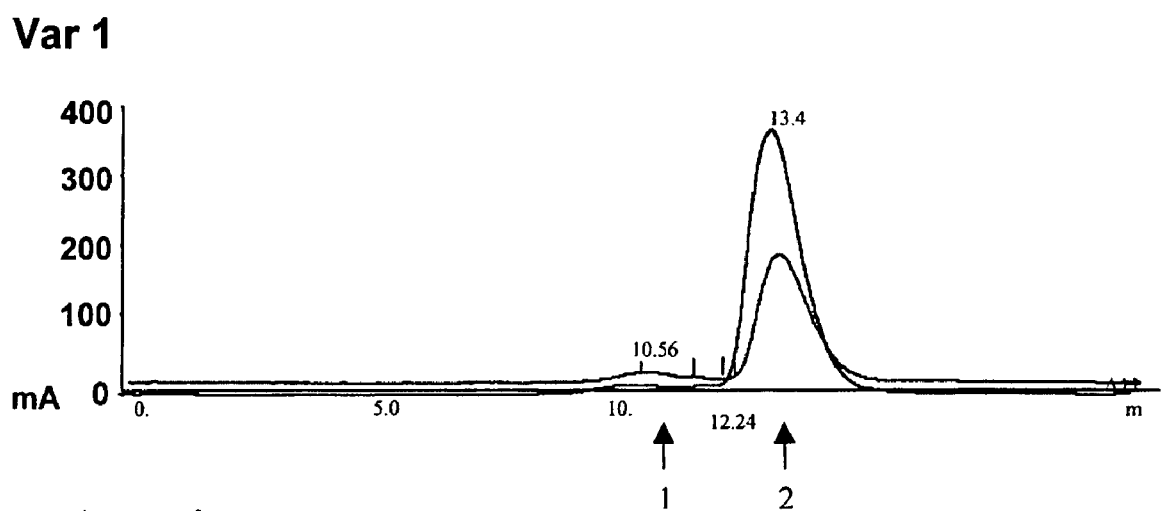

The G-CSF variant (Var 1) produced soluble monomeric protein, with a yield of 8 mg/L as shown in FIG. 3. The wild-type produced no monomeric protein and a small amount, 8 μg/L of dimeric or aggregated G-CSF (FIG. 3).

Example 9

Biological Activity of G-CSF

The biological activity of variant and wild type was assessed in a OCI/AML5 cell proliferation assay. OCI/AML5 cells were obtained from the German collection of Microorganisms and cell culture (DSMZ, Braunschweig. ACC 247) and maintained according to supplied protocols. Assay media comprised MEMA containing 16.6% v/v foetal bovine serum. Prior to each assay, OCI/AML5 cells were pelleted by centrifugation at 300×g for 5 mins, the media removed by aspiration and the cells resuspended in assay media. This process was repeated three additional times with cells resuspended at a final concentration of 1×105/ml in assay media. G-CSF variants (in duplicate) were diluted to the desired concentrations in assay media. 100 ul of resuspended cells were then added to each assay point to give a total assay volume of 200 ul/well. Assay plates were incubated at 37 C was for 72 hours at 37 C under 5% CO2. 20 ul of tritiated thymidine (5 Ci/ml, NEN) was then added to each assay point and assay plates were returned to the incubator for a further 4 hours. Cells were harvested on glass fibre filter plates (Perkin Elmer) using a cell harvester. Thymidine incorporation was determined using a Packard TopCount microplate liquid scintillation counter. Data were analysed using Graphpad Prism software.

G-CSF variant Var 1 was more active than wild-type G-CSF in the OC1/AML5 proliferation assay (Table 3).

TABLE 3

| $EC_{50}$ of G-CSF wild-type (WT) and variant Var 1 in the OC1/AML5 proliferation assay. ||
| --- | --- |
| Sample | $EC_{50}$ (nM) |
| WT | 6 |
| Var. 1 | 2.6 |

Sequence Analysis of G-CSF Variant

The variant Var. 1 was sequenced. The sequence of the variant is described below as differences at the amino acid level from WT G-CSF having the amino acid sequence shown in SEQ ID No 6.

```
                                              (SEQ ID NO: 16)
Var. 1     C17G W58R Q70R F83L
```

```
SEQ ID NO: 1 Nucleotide sequence encoding WT human EPO
SEQ ID NO: 2 Amino acid sequence of WT human EPO
GCCCCACCACGCTTCATCTGTGACAGCCGAGTCCTGGAGAGGTACCTCTTGGAGGCCAAG
CGGGGTGGTGCGAAGTAGACACTGTCGGCTCAGGACCTCTCCATGGAGAACCTCCGGTTC
 A   P   P   R   F   I   C   D   S   R   V   L   E   R   Y   L   L   E   A   K
                                       10                                  20

GAGGCCGAGAATATCACGACGGGCTGTGCTGAACACTGCAGCTTGAATGAGAATATCACT
CTCCGGCTCTTATAGTGCTGCCCGACACGACTTGTGACGTCGAACTTACTCTTATAGTGA
 E   A   E   N   I   T   T   G   C   A   E   H   C   S   L   N   E   N   I   T
                                       30                                  40

GTCCCAGACACCAAAGTTAATTTCTATGCCTGGAAGAGGATGGAGGTCGGGCAGCAGGCC
CAGGGTCTGTGGTTTCAATTAAAGATACGGACCTTCTCCTACCTCCAGCCCGTCGTCCGG
 V   P   D   T   K   V   N   F   Y   A   W   K   R   M   E   V   G   Q   Q   A
                                       50                                  60

GTAGAAGTCTGGCAGGGCCTGGCCCTGCTGTCGGAAGCTGTCCTGCGGGGCCAGGCCCTG
CATCTTCAGACCGTCCCGGACCGGGACGACAGCCTTCGACAGGACGCCCCGGTCCGGGAC
 V   E   V   W   Q   G   L   A   L   L   S   E   A   V   L   R   G   Q   A   L
                                       70                                  80

TTGGTCAACTCTTCCCAGCCGTGGGAGCCCCTGCAGCTGCATGTGGATAAAGCCGTCAGT
AACCAGTTGAGAAGGGTCGGCACCCTCGGGGACGTCGACGTACACCTATTTCGGCAGTCA
 L   V   N   S   S   Q   P   W   E   P   L   Q   L   H   V   D   K   A   V   S
                                       90                                 100
```

```
GGCCTTCGCAGCCTCACCACTCTGCTTCGGGCTCTGGGAGCCCAGGAGGAAGCCATCTCC
CCGGAAGCGTCGGAGTGGTGAGACGAAGCCCGAGACCCTCGGGTCCTCCTTCGGTAGAGG
 G   L   R   S   L   T   T   L   L   R   A   L   G   A   Q   E   E   A   I   S
                         110                                          120

CCTCCAGATGCGGCCTCAGCTGCTCCACTCCGAACAATCACTGCTGACACTTTCCGCAAA
GGAGGTCTACGCCGGAGTCGACGAGGTGAGGCTTGTTAGTGACGACTGTGAAAGGCGTTT
 P   P   D   A   A   S   A   A   P   L   R   T   I   T   A   D   T   F   R   K
                         130                                          140

CTCTTCCGAGTCTACTCCAATTTCCTCCGGGGAAAGCTGAAGCTGTACACAGGGGAGGCC
GAGAAGGCTCAGATGAGGTTAAAGGAGGCCCCTTTCGACTTCGACATGTGTCCCCTCCGG
 L   F   R   V   Y   S   N   F   L   R   G   K   L   K   L   Y   T   G   E   A
                         150                                          160

TGCAGGACAGGGGACAGA
ACGTCCTGTCCCCTGTCT
 C   R   T   G   D   R

SEQ ID NO: 3 Nucleotide sequence encoding WT human GM-CSF
SEQ ID NO: 4 Amino acid sequence of WT human GM-CSF
GCACCCGCCCGCTCGCCCAGCCCCAGCACGCAGCCCTGGGAGCATGTGAATGCCATCCAG
CGTGGGCGGGCGAGCGGGTCGGGGTCGTGCGTCGGGACCCTCGTACACTTACGGTAGGTC
 A   P   A   R   S   P   S   P   S   T   Q   P   W   E   H   V   N   A   I   Q>
                         10                                           20

GAGGCCCGGCGTCTCCTGAACCTGAGTAGAGACACTGCTGCTGAGATGAATGAAACAGTA
CTCCGGGCCGCAGAGGACTTGGACTCATCTCTGTGACGACGACTCTACTTACTTTGTCAT
 E   A   R   R   L   L   N   L   S   R   D   T   A   A   E   M   N   E   T   V>
                         30                                           40

GAAGTCATCTCAGAAATGTTTGACCTCCAGGAGCCGACCTGCCTACAGACCCGCCTGGAG
CTTCAGTAGAGTCTTTACAAACTGGAGGTCCTCGGCTGGACGGATGTCTGGGCGGACCTC
 E   V   I   S   E   M   F   D   L   Q   E   P   T   C   L   Q   T   R   L   E>
                         50                                           60

CTGTACAAGCAGGGCCTGCGGGGCAGCCTCACCAAGCTCAAGGGCCCCTTGACCATGATG
GACATGTTCGTCCCGGACGCCCCGTCGGAGTGGTTCGAGTTCCCGGGGAACTGGTACTAC
 L   Y   K   Q   G   L   R   G   S   L   T   K   L   K   G   P   L   T   M   N>
                         70                                           80

GCCAGCCACTACAAGCAGCACTGCCCTCCAACCCCGGAAACTTCCTGTGCAACCCAGATT
CGGTCGGTGATGTTCGTCGTGACGGGAGGTTGGGGCCTTTGAAGGACACGTTGGGTCTAA
 A   S   H   Y   K   Q   H   C   P   P   T   P   E   T   S   C   A   T   Q   I>
                         90                                           100

ATCACCTTTGAAAGTTTCAAAGAGAACCTGAAGGACTTTCTGCTTGTCATCCCCTTTGAC
TAGTGGAAACTTTCAAAGTTTCTCTTGGACTTCCTGAAAGACGAACAGTAGGGGAAACTG
 I   T   F   E   S   F   K   E   N   L   K   D   F   L   L   V   I   P   F   D>
                         110                                          120

TGCTGGGAGCCAGTCCAGGAG
ACGACCCTCGGTCAGGTCCTC
 C   W   E   P   V   Q   E>

SEQ ID NO: 5 Nucleotide sequence encoding WT human G-CSF
SEQ ID NO: 6 Amino acid sequence of WT human G-CSF
ACCCCCCTGGGCCCTGCCAGCTCCCTGCCCCAGAGCTTCCTGCTCAAGTGCTTAGAGCAA
TGGGGGGACCCGGGACGGTCGAGGGACGGGGTCTCGAAGGACGAGTTCACGAATCTCGTT
 T   P   L   G   P   A   S   S   L   P   Q   S   F   L   L   K   C   L   E   Q
                         10                                           20

GTGAGGAAGATCCAGGGCGATGGCGCAGCGCTCCAGGAGAAGCTGTGTGCCACCTACAAG
CACTCCTTCTAGGTCCCGCTACCGCGTCGCGAGGTCCTCTTCGACACACGGTGGATGTTC
 V   R   K   I   Q   G   D   G   A   A   L   Q   E   K   L   C   A   T   Y   K
                         30                                           40

CTGTGCCACCCCGAGGAGCTGGTGCTGCTCGGACACTCTCTGGGCATCCCCTGGGCTCCC
GACACGGTGGGGCTCCTCGACCACGACGAGCCTGTGAGAGACCCGTAGGGGACCCGAGGG
 L   C   H   P   E   E   L   V   L   L   G   H   S   L   G   I   P   W   A   P
                         50                                           60

CTGAGCAGCTGCCCCAGCCAGGCCCTGCAGCTGGCAGGCTGCTTGAGCCAACTCCATAGC
GACTCGTCGACGGGGTCGGTCCGGGACGTCGACCGTCCGACGAACTCGGTTGAGGTATCG
 L   S   S   C   P   S   Q   A   L   Q   L   A   G   C   L   S   Q   L   H   S
                         70                                           80

GGCCTTTTCCTCTACCAGGGGCTCCTGCAGGCCCTGGAAGGGATCTCCCCCGAGTTGGGT
CCGGAAAAGGAGATGGTCCCCGAGGACGTCCGGGACCTTCCCTAGAGGGGGCTCAACCCA
 G   L   F   L   Y   Q   G   L   L   Q   A   L   E   G   I   S   P   E   L   G
```

```
CCCACCTTGGACACACTGCAGCTGGACGTCGCCGACTTTGCCACCACCATCTGGCAGCAG
GGGTGGAACCTGTGTGACGTCGACCTGCAGCGGCTGAAACGGTGGTGGTAGACCGTCGTC
  P   T   L   D   T   L   Q   L   D   V   A   D   F   A   T   T   I   W   Q   Q
                        110                                         120

ATGGAAGAACTGGGAATGGCCCCTGCCCTGCAGCCCACCCAGGGTGCCATGCCGGCCTTC
TACCTTCTTGACCCTTACCGGGGACGGGACGTCGGGTGGGTCCCACGGTACGGCCGGAAG
  M   E   E   L   G   M   A   P   A   L   Q   P   T   Q   G   A   M   P   A   F
                        130                                         140

GCCTCTGCTTTCCAGCGCCGGGCAGGAGGGGTCCTGGTTGCCTCCCATCTGCAGAGCTTC
CGGAGACGAAAGGTCGCGGCCCGTCCTCCCCAGGACCAACGGAGGGTAGACGTCTCGAAG
  A   S   A   F   Q   R   R   A   G   G   V   L   V   A   S   H   L   Q   S   F
                        150                                         160

CTGGAGGTGTCGTACCGCGTTCTACGCCACCTTGCCCAGCCC
GACCTCCACAGCATGGCGCAAGATGCGGTGGAACGGGTCGGG
  L   E   V   S   Y   R   V   L   R   H   L   A   Q   P
                        170
```

---

The invention claimed is:

1. A method of providing a subject polypeptide variant with improved stability compared with a parent subject polypeptide, the method comprising:
   (a) providing mRNA molecules, each mRNA molecule comprising a nucleotide sequence encoding a subject polypeptide variant and lacking an in-frame stop codon;
   (b) incubating the mRNA molecules under conditions for ribosome translation of the mRNA molecules to produce encoded subject polypeptide variants, whereby complexes each comprising at least a ribosome, mRNA and encoded subject polypeptide variant are formed;
   (c) bringing the complexes into contact with a receptor, ligand or specific binding pair member that binds the parent subject polypeptide, and selecting one or more complexes each displaying a subject polypeptide variant able to bind the receptor, ligand or specific binding pair member under the conditions of the selection;
   wherein dithiothreitol (DTT) is applied as a stability selection pressure during translation in step (b) and continues to be applied during selecting in step (c), and hydrophobic interaction chromatography (HIC) and room temperature are applied simultaneously with DTT as further stability selection pressures during selecting in step (c), or are applied simultaneously with DTT after translation in step (b) and removed prior to bringing the complexes into contact with the receptor, ligand or specific binding pair member in step (c); and
   (d) determining stability of selected subject polypeptide variant or variants, whereby one or more subject polypeptide variants with improved stability compared with the parent subject polypeptide are obtained.

2. The method according to claim 1, wherein stability is determined by comparing ability of selected subject polypeptide variant or variants to bind receptor, ligand or specific binding pair member when displayed, when produced in the presence and absence of DTT.

3. The method according to claim 1, wherein stability is determined by comparing aggregation of selected subject polypeptide variant or variants with that of the parent subject polypeptide.

4. The method according to claim 1 wherein mRNA molecules for incubation in the translation system are provided by means of RT-PCR reactions in which at least one RT-PCR primer is a mutagenic primer encoding a diversity of different sequences for inclusion in a defined region of the nucleotide sequence encoding a subject polypeptide variant.

5. The method according to claim 1 further comprising retrieving mRNA from a selected complex.

6. The method according to claim 5 wherein mRNA retrieved from a selected complex displaying a selected subject polypeptide variant is amplified and copied into DNA encoding the selected subject polypeptide variant.

7. The method according to claim 6 wherein the DNA is provided in an expression system for production of a product, which product is the selected subject polypeptide variant or a polypeptide chain of the selected subject polypeptide variant.

8. The method according to claim 7 further comprising isolating or purifying the product.

9. The method according to claim 8 further comprising formulating the product into a composition comprising at least one additional component.

10. The method according to claim 6 wherein DNA encoding the selected subject polypeptide variant or a polypeptide chain of the selected subject polypeptide variant is provided within a nucleotide sequence to provide a nucleotide sequence encoding a fusion protein comprising the selected subject polypeptide variant, or a polypeptide chain of the selected subject polypeptide variant, fused to additional amino acids.

11. The method according to claim 10 wherein DNA comprising said nucleotide sequence encoding said fusion protein is provided in an expression system for production of a product, which product is the fusion protein.

12. The method according to claim 11 further comprising isolating or purifying the product.

13. The method according to claim 12 further comprising formulating the product into a composition comprising at least one additional component.

14. The method according to claim 6 wherein DNA encoding the selected subject polypeptide variant or a polypeptide chain of the selected subject polypeptide variant is mutated to encode a polypeptide that comprises an amino acid sequence that differs from the selected subject polypeptide variant or polypeptide chain of the selected subject polypeptide variant.

15. The method according to claim 14 wherein mutated DNA encoding said polypeptide is provided in an expression system for production of a product, which product is said polypeptide.

16. The method according to claim 15 further comprising isolating or purifying the product.

17. The method according to claim 16 further comprising formulating the product into a composition comprising at least one additional component.

18. The method according to claim 1, wherein the parent subject polypeptide is an antibody molecule.

19. The method according to claim 18, wherein the antibody molecule is a single chain antibody molecule.

20. The method according to claim 19, wherein the antibody molecule is a scFv, $V_H$, Fd or dAb molecule.

21. The method according to claim 1, wherein the parent subject polypeptide is a member of the family of four antiparallel α-helix bundle proteins.

22. The method according to claim 1, wherein the parent subject polypeptide is an extracellular domain of a complex receptor.

23. The method according to claim 1, wherein the parent subject polypeptide is an erythropoietin (EPO).

24. The method according to claim 23, wherein the parent subject polypeptide is human wild-type EPO having the sequence shown in SEQ ID NO: 2.

25. The method according to claim 24, wherein a subject polypeptide variant comprises a set of mutations in the human wild-type sequence of SEQ ID NO: 2 selected from the group consisting of the following sets of mutations:
  (1) L16I I25F T27M V61A R139H T157V (SEQ ID NO: 10)
  (2) D8V T26A T27A S126P G158E (SEQ ID NO: 11)
  (3) D8V T27A Y49N W64R V82A E89G S126P G158E (SEQ ID NO: 12)
  (4) T26A W64R A135V G158E (SEQ ID NO: 13)
  (5) D8V V74F T107A N147D (SEQ ID NO: 14).

26. The method according to claim 1, wherein the parent subject polypeptide is a granulocyte-macrophage colony stimulating factor (GM-CSF).

27. The method according to claim 26, wherein the parent subject polypeptide is human wild-type GM-CSF having the sequence shown in SEQ ID NO: 4.

28. The method according to claim 27, wherein a subject polypeptide variant comprises a set of mutations:
  R4S H15L A18V I43V K63T T102A (SEQ ID NO: 15)
in the human wild-type sequence of SEQ ID NO: 4.

29. The method according to claim 1, wherein the parent subject polypeptide is a granulocyte colony stimulating factor (G-CSF).

30. The method according to claim 29, wherein the parent subject polypeptide is human wild-type G-CSF having the sequence shown in SEQ ID NO: 6.

31. The method according to claim 30, wherein a subject polypeptide variant comprises a set of mutations:
  C17G W58R Q70R F83L (SEQ ID NO: 16)
in the human wild-type sequence of SEQ ID NO: 6.

32. A method of producing a subject polypeptide variant that has improved stability compared with a parent subject polypeptide, the method comprising:
  producing a subject polypeptide variant in a ribosome display system by expression from encoding nucleic acid in the presence and absence of DTT; and
  testing for improved stability by comparison of binding using hydrophobic interaction chromatography at room temperature of the subject polypeptide variant to cognate receptor, ligand or specific binding pair member when displayed on ribosomes and produced in the presence and absence of DTT.

33. The method of claim 32, wherein stability is tested using as a measure of stability the ratio of binding activity to subject polypeptide receptor, ligand or specific binding pair member when translated in the presence of DTT in a radioimmunoassay and of binding activity to subject polypeptide receptor, ligand or specific binding pair member when translated in the absence of DTT in the same assay.

34. The method according to claim 32 comprising the step of isolating the subject polypeptide variant prior to the testing.

35. The method according to claim 32 comprising mutating nucleic acid encoding a parent subject polypeptide, to provide a nucleic acid encoding a subject polypeptide variant prior to expression therefrom.

36. A method of identifying or obtaining a subject polypeptide variant which has improved stability compared with a parent subject polypeptide, the method comprising:
  mutating nucleic acid encoding the parent subject polypeptide, to provide one or more nucleic acids with sequences encoding one or more subject polypeptide variants with altered amino acid sequences;
  expressing the nucleic acid or nucleic acids to produce the subject polypeptide variant or variants in a ribosome display system, in the presence and absence of DTT; and
  testing the subject polypeptide variant or variants thus produced for improved stability compared with parent subject polypeptide, by comparing by means of hydrophobic interaction chromatography performed at room temperature binding for cognate receptor, ligand or specific binding member of subject polypeptide variant displayed on ribosomes produced in the presence and absence of DTT.

37. The method according to claim 36 comprising producing a library of subject polypeptide variants and testing the variants of said library for improved stability.

38. The method according to claim 37 comprising identifying one or more subject polypeptide variants with improved stability.

39. The method according to claim 38 comprising isolating said one or more subject polypeptide variants.

40. The method according to claim 38 comprising isolating nucleic acid sequence encoding said one or more subject polypeptide variants.

41. The method according to claim 40 comprising formulating said one or more isolated subject polypeptide variants into a composition comprising at least one additional component.

* * * * *